United States Patent
Lander et al.

(10) Patent No.: US 12,128,246 B2
(45) Date of Patent: Oct. 29, 2024

(54) METHOD AND APPARATUS FOR TREATMENT OF VIRAL INFECTIONS

(71) Applicants: Victor Lander, Short Hills, NJ (US); Jacob Gitman, Bay Harbor Island, FL (US)

(72) Inventors: Victor Lander, Short Hills, NJ (US); Jacob Gitman, Bay Harbor Island, FL (US)

(*) Notice: Subject to any disclaimer, the term of this patent is extended or adjusted under 35 U.S.C. 154(b) by 0 days.

(21) Appl. No.: 17/803,294

(22) Filed: Apr. 28, 2022

(65) Prior Publication Data
US 2024/0001137 A1    Jan. 4, 2024

(51) Int. Cl.
*A61N 5/02*    (2006.01)
*A61N 5/04*    (2006.01)

(52) U.S. Cl.
CPC ............... *A61N 5/022* (2013.01); *A61N 5/04* (2013.01); *A61N 2005/027* (2013.01)

(58) Field of Classification Search
CPC ..... A61N 5/022; A61N 5/04; A61N 2005/027
See application file for complete search history.

(56) References Cited

U.S. PATENT DOCUMENTS

| | | | | |
|---|---|---|---|---|
| 5,097,844 A | * | 3/1992 | Turner | A61N 5/02 600/549 |
| 5,810,888 A | * | 9/1998 | Fenn | A61K 41/0052 600/407 |
| 6,330,479 B1 | * | 12/2001 | Stauffer | A61B 5/0507 607/101 |
| 2003/0018277 A1 | * | 1/2003 | He | A61B 5/318 600/544 |
| 2013/0149192 A1 | * | 6/2013 | Keady | A61L 2/0029 422/127 |
| 2020/0345873 A1 | * | 11/2020 | Ashrafi | A61N 5/0624 |

* cited by examiner

*Primary Examiner* — Michael F Peffley
*Assistant Examiner* — Bo Ouyang
(74) *Attorney, Agent, or Firm* — Henry M. Feiereisen LLC

(57) ABSTRACT

The Method for the treatment of patients with viral infections such as COV-2-BARS or others using Microwave Resonant Absorption (MRA) effect in viruses and based on Structure Resonant Energy Transfer (SRET) that causes Confined Acoustic Vibrations (CAV) in infectious viruses and, as a result, their destruction. Devices using coupling of multi-frequency microwave energy to the patient organs infected with virus with Near Field Focused (NFF) antenna arrays, implemented to irradiate infected organs such as lungs, larynx, and nasofarinx by exciting high amplitude acoustic vibrations to fracture the outer protein shell (capsid) of the virus and completely or, at least, partially inactivate it.

10 Claims, 16 Drawing Sheets

Figure 1:
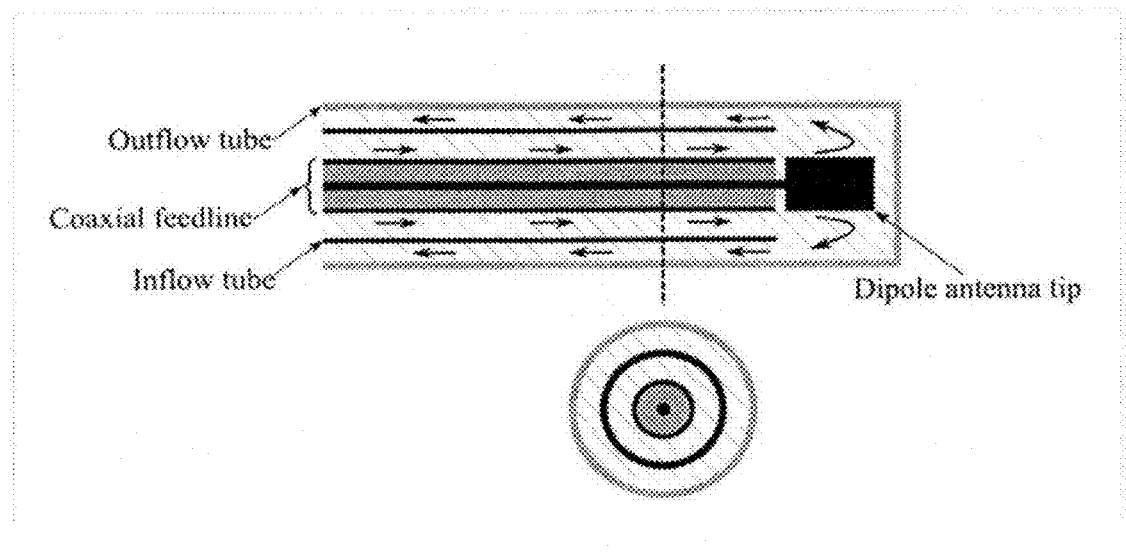

| 1 | 2 | 3 | 4 |
|---|---|---|---|
| Determine the type of the virus and its main parameters to cause capsid lyses: -Acoustic Resonant Frequency -Destruction Threshold Power Density | Construct 3-D model of the organ under the treatment using X-ray or MRI or other methods. | Create theoretical model of EM wave propagation from NFF antenna array positioned outside of the body through body layers reaching the organ to be irradiated. | Develop 3-D map for NFF antenna spot movement inside of the organ and stored data for phase and amplitude of array elements for each focal spot position. |

| 8 | 7 | 6 | 5 |
|---|---|---|---|
| Start treatment procedure, while monitoring surrounding tissue temperature | On array controllers synchronize movement of focal spot of irradiation array with movement of focal spot of temperature monitoring array | Select the appropriate NFF array for microwave temperature monitoring by radiometer. | Select the appropriate NFF array(s). Preprogram the beam-former processor for focal spot movement in space and time using 3-D map. |

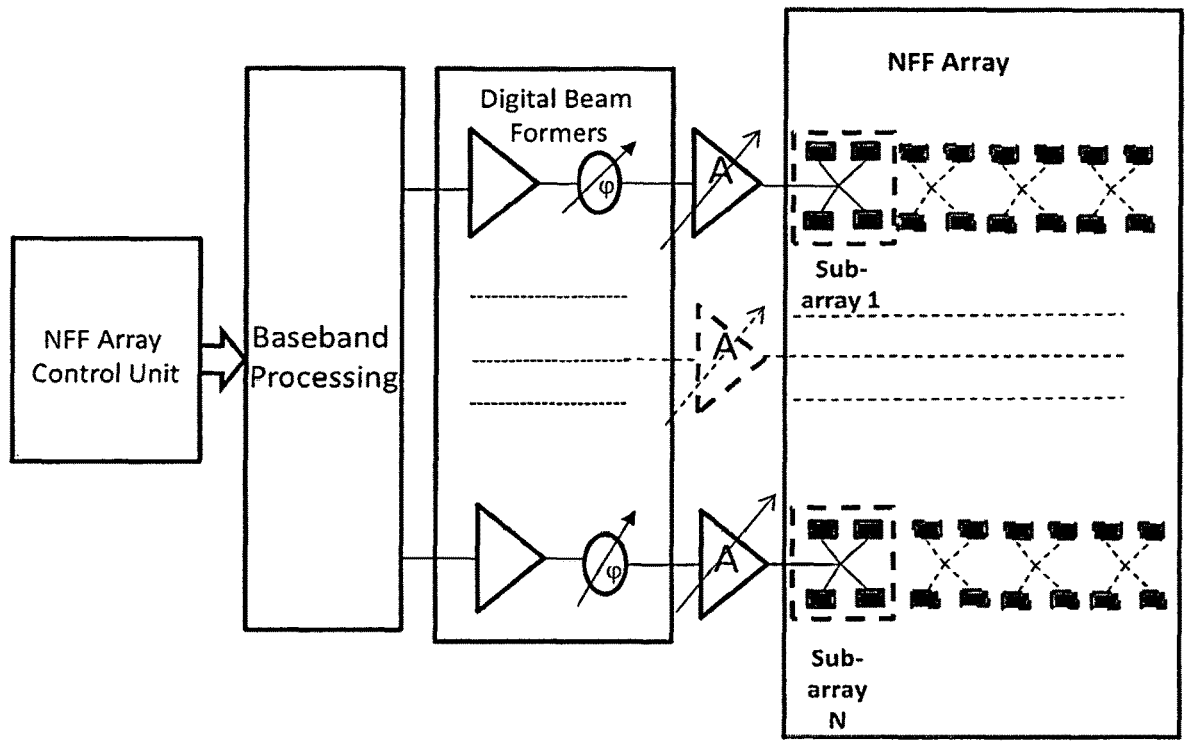
Fig. 14
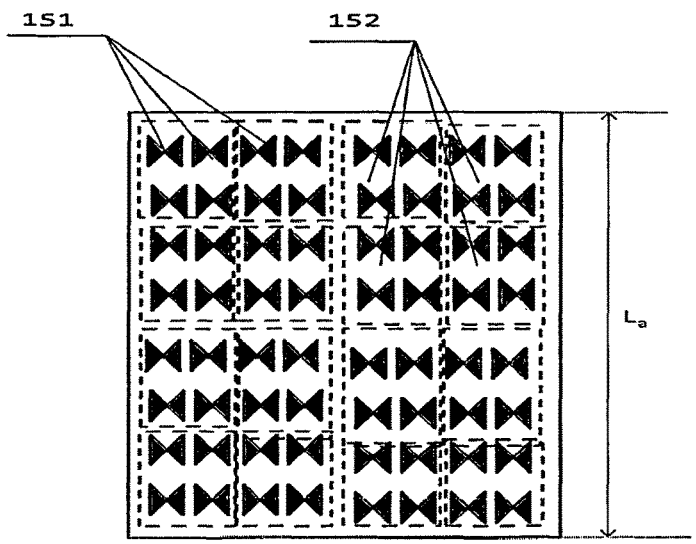
Fg. 15

METHOD AND APPARATUS FOR TREATMENT OF VIRAL INFECTIONS

BACKGROUND OF THE INVENTION

The present invention relates to methods and apparatuses for eradication or at least weakening of viral infections from humaR patients.

Pandemic outbreaks cause tremendous moral, physical, and financial stress on human population and health industry of the world. During the last years significant efforts have been made to eradicate different viruses with variable success. The latest mutations of Severe Acute Respiratory Syndrome (SARS) corona viruses demonstrated extremely high rate of infections by COVID-19 variants. Different methods of epidemic prevention have been tried starting from simple ordering of safe distancing and wearing masks and ending with complete lockdown of the offices, cities, and even countries.

Besides the population vaccination, different methods of space sterilization from virus have been made, such as chemical inactivation, UV irradiation, and microwave thermal heating. All these methods cannot be allowed in the public presence because of the harmful effects of the UV radiation or extremely high field strength requirements for microwave space heating to be effective. For example, in one of the studies [5] conducted using microwave oven, it was demonstrated 100% inactivation of airborne MS2 virus in the air transmitting 700 W of power at 2.45 GHz. It corresponds to electrical field amplitude E=514 V/M, which is prohibitively high for human presence. Insufficient infection prevention attempts causes high level of acute SARS syndrome and in many cases resulted in such drastic measures as an intubation of the patient and using medications with severe side effects.

Continuing intensive studies of the virus structure by scientific community discovered that the virus is essentially a protein ball with genomes packed inside. The existence of electrical charges present in the virus core was also discovered as well as mechanical resonance frequency at which these charges can oscillate inside of the virion capsid.

One of the first publications on this subject was the work of Y. Robach et. all [1], who in 1983 discovered the evidence of ultrasonic absorption causing structural fluctuations inside of the capsid of the virus that infects frogs. In 2000 M. Babincova et. all [2] suggested a possibility of using resonant absorption of ultrasound energy as a method of HIV destruction. In 2009 Liu Tzu Ming [4] demonstrated possibility of resonant absorption of energy through dipolar coupling of EM waves with confined acoustic vibrations. In this seminal work authors showed that by using Lamb's equation for dipolar coupling, the frequencies of corresponding dipolar modes can be calculated:

$$4*[J_2(\xi)/J_1(\xi)]-\eta^2+2*[J_2(\xi)/J_1(\xi)]*\eta=0, \quad (1)$$

where, $J_n$ are spherical Bessel functions of the first kind;
$\xi=\omega*R/V_l$;
$\eta=\omega*R/V_t$;
$V_l$ and $V_t$ are longitudinal and transverse sound velocities in the virion;
$\omega$ is an angular frequency of the vibration mode;
R is a radius of a virion's shell (capsid) modeled as a sphere.

When the oscillating EM field is applied to the viral particle, which can be represented by nano-sphere, opposite charges displacements between core and capsid can be produced and different dipolar acoustic vibration modes can be generated. Out of all types of modes that can be excited in core-shell vibrating system, only a dipolar spherical mode can be directly coupled to EM wave, whose wavelength is much longer than the particle size. Solving (1) for resonant frequency f one can find [6]

$$f=V_l/2*D, \quad (2)$$

where D is a diameter of the sphere.

From scattering parameters measurements and using electronic microscopes the diameter of spherical viruses has been estimated. For example, considering that $V_l$ for a typical virus is in the range of 1500-2000 m/sec, and a measured diameter of the tobacco virus D=17 nm, the estimated resonant frequency for this virus is in the range of 30 GHz to 40 GHz [4].

In [3] has been experimentally shown that a virus H3N2 Influenza Type A has Microwave Resonant Absorption (MRA) frequency of 8.2 GHz. From published [3], [4], parameters of this typical SARS virus, the threshold magnitude of electric field $E_{th}$ to fracture the capsid of the virus was calculated. The results shown in [4] carry a strong resonant characteristic with a minimum value of destructive electric field $E_{th}$=86.9 V/m centered at 8.2 GHz.

If major physical parameters of the virus are known or measured, the required destructive threshold electrical field $E_{th}$ can be found from the expression (3) [6], [3]:

$$E_{th}=P_{th}\pi r^2(SQRT(m^*(\omega_0^2-\omega^2)+(\omega_0 m^*)/Q)^2\omega^2)/(3.45qm^*\omega^2), \quad (3)$$

where $P_{th}$—a threshold stress for a membrane fracturing,
r-spherical radius of virus,
m*-reduced mass of virus,
Q-quality factor,
q-electrical charge,
$\omega_0$-MRA resonant circular frequency.

After the value for $E_{th}$ is obtained from (3), a free space power density required to create the threshold electrical field can be found (4):

$$P_{th}^0=E_{th}^2/Z_0, \quad (4)$$

where $Z_0$ is a free space impedance, $Z_0$=377 ohm.

However, at the same time, the experimentally obtained value of $P_{th}^0$ for 100% virus inactivation in glass slides or glass viles with samples H3N2 was about 810 W/m², which corresponds to an electric field magnitude 3 times higher than the theoretical value of $E_{th}$. In [6] the authors concluded that for SARS-CoV-2 virus theoretical values for the threshold electric field magnitude is $E_{th}$=24+/−3 V/m, the corresponding free space power density $P_{th}$=1.5 +/−0.4 W/m², and MRA frequency $f_a$=10-17 GHz. Considering that at the threshold field intensity, only 38% of the viral population has been inactivated, the recommendation was made in [6] to use the power density approximately 10 times higher than the threshold value: 14.5 W/m² (E=74 V/m) for 100% eradication of viral load of SARS-CoV-2 up to 7.5*10¹⁴ m⁻³.

Results of calculations of resonant frequency for different viruses are shown in Table 1.

TABLE 1

| Virus | Diameter, nm | Resonant Frequency, GHz | Source |
| --- | --- | --- | --- |
| Influenza A | 100 | 8.2-12.9 | [3] |
| EV71 | 28.5-35 | 34-42 | [3] |
| SARS-CoV-2, Compete Range | 100 60-140 | 8.2-20 | [7], [6] |

It is important to note that biological cells can tolerate 50-150 W/m² microwave power density without developing a thermal stress [25]. Epithelial cells can tolerate non-ionizing MW radiation with power density of 10 W/m² applied over 24 hours [10]. Therefore the irradiation of the treated organ with power density of 10-14.5 W/m 2 over the session of 15 minutes should not produce any harmful effects on the patient. As it will be shown further, the significant losses in human body tissues will require a large amount of microwave power to be applied to an external surface to achieve a desirable power density in the organ under the treatment. Water cooling boluses, similar to those used for the hyperthermia treatment, can be used for the proposed treatment against viral infections.

The latest research on virions density in infected organs [32] shows that initially it is concentrated in the nasal cavities ($10^5$-$10^6$)/g, then in throat larynges ($10^7$-$10^8$)/g, and the most of it later infects lungs ($10^8$-$10^{10}$)/g, thus making it extremely important to inactivate virions in these organs during initial and middle stages of person's infection. The proposed invention describes method and devices for viral load destruction in lungs, larynges, and nasal cavities using focused microwave antenna arrays capable of steerable microwave radiation at Structural Acoustic Resonance (SAR) frequency and delivering a power above the threshold causing virions capsid lyses and, consequently, virus deactivation. Near Field Focused (NFF) array utilization will minimize the power requirements at the source by creating a high density concentration of EM power at the focal spot and to provide means for 3D movement of this spot to cover a full volume of the treated organ.

As for the Prior Art, the following methods have been implemented. Contemporary methods of microwave medical treatment and applications can be divided on two major fields: microwave imaging and microwave hyperthermia.

One class of them is transcutaneous instruments for using tissue heating properties of microwave irradiation, which are all based on a local small area "microwave oven" effect. Multiple examples of tools and methods of this kind of treatment can be found in [10]. They are utilized for treatment of different organs using localized heating—ablation method. The main instruments for these methods are low profile thin antennas in shape of a needle and operating mostly at frequency 2.45 GHz. The idea of these methods is to deliver high level of microwave energy to small area in the organ (typically malignant tumor) in order to destroy the cells by microwave heating (ablation) phenomenon.

One example of a typical design of an ablation antenna with liquid cooling to preserve surrounding tissues is shown in FIG. 1. A thin radiator assembly consist of a radiating tip and a flexible coaxial tubing for transmission of microwave power and cooling liquid supply. The assembly is inserted into a large blood vessel, urethra, or any other way to position the radiator near the treatment organ. As it can be easily seen from its design, it cannot be implemented for a large area external irradiation for viral sterilization.

Another example of a breast tumor treatment is described in U.S. Pat. No. 9,387,036 issued to Turner et. al. In this patent the small balloon with ionized water was inserted in the breast near the tumor and was used as an absorption target to create higher temperature zone of +45 degrees C. while the breast was irradiated by microwave frequency 915 MHz. The described method and device are not suitable for creating SAR in the viruses and for treatment of COVID-2-SARS patients because of its' body intervention requirements.

An example of an external microwave body irradiation is described in U.S. Pat. No. 8,068,919 issued to Ran where "the methods and apparatus involve use of microwave source (or sources) that outputs multiple microwaves that are non-correlated with each other in phase; an array of antennas that radiate substantially plane microwaves to form a pseudo uniform microwave electromagnetic field, where the microwaves are not phase-correlated, in order to eliminate non-uniform heating caused by interference." As it is stipulated in the citation, the idea is to use non-correlated waves which are not suitable for steerable focused beam radiation, which is required for creation of high density EM energy spot on the internal organs simultaneously protecting the external body layers from harmful radiation levels.

In U.S. Pat. No. 5,492,122 to Button et al. the MRI-RF a combination of a setup and a method was described. The method utilizes MRI setup for localization of the focal point of large cylindrical antenna array positioned around MRI coils. The method can be useful for hyperthermia tumors treatments with high precision using L-band of microwave spectrum. It is not applicable for virus destruction because of very high microwave frequencies are required for MRA and very large diameter of circular array suggested in the Patent, which prevents it application for COVID-2-SARS virus destruction.

One example of implementation of ionizing non-targeted radiation for COVID-19 patient treatment in critical stage was published in [19]. In this case the 80% success of treatment of patients in critical condition was achieved by lung area irradiation by radioactive isotopes with risk of destruction of the healthy cells as well as a risk of cancer as a side effect. The important results confirmed the possibility of complete recovery of COVID-19 patients even in critical condition after eradication of the virus in lungs area.

Figure 2:
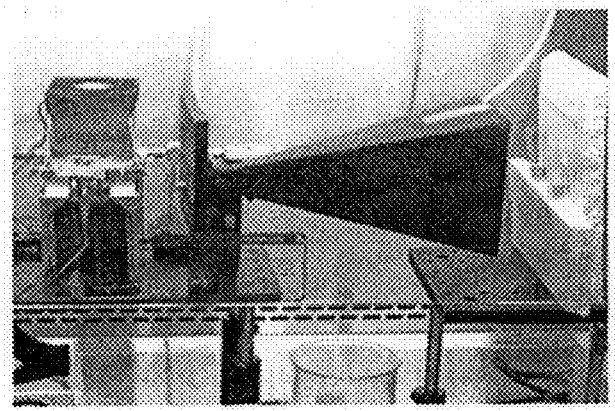

In another example of implementation of microwave energy authors [3] described a setup for virus inactivation using Confined Acoustic Vibration at SAR frequency. FIG. 2 shows experimental setup demonstrated in [3] where the vials with virus have been irradiated from the standard microwave horn antenna with samples positioned in Near Zone of the antenna field. In order to achieve a healing effect on internal organ located deep inside of the body and infected by virus, this setup must produce very high density radiation field in order to compensate for significant losses in external tissues such as skin, muscles, and fat. These types of setup cannot create focused field concentration required for treatment of organs inside of the human body because it irradiates a large area in the antenna near zone with exponentially lower field density at further distance from antenna. It is obvious that simple horn antenna cannot provide targeted irradiation of human organs deep in the body such as lungs or throat larynges.

The focal antenna array of circular design has been offered in [29] and [30]. These arrays also were operating at very low microwave frequencies and have been using Far Zone focusing requiring significant microwave power to penetrate external body layers.

U.S. Patent Application 2003/0088180 describes a focused antenna array used for microwave imaging of cancerous tumors detection. Application suggests algorithm for reflections cancellation using steerable focused property of array with improved accuracy for detecting received signals from tumor using pulsed signals. The application does not describe a steerable high power transmission required for COVID virus SAR fracture at high microwave frequency.

U.S. Pat. No. 5,492,122 describes an apparatus used for cancer tumors' treatment using a microwave hyperthermia. In this patent "Antenna elements polarized parallel to the axis of the cylinder are used for forming a Specific Absorption Ratio (SAR) map as well as for directing the energy to accomplish hyperthermia. The array may be dynamically controlled to focus energy at any specified region within the cylinder. The array is positioned inside an MRI machine and is tuned to the machine's hydrogen resonant frequency." The hydrogen nuclei in a typical 1.5-3 T MRI magnetic field strength have a resonant frequency of approximately 64 MHz-100 MHz which used in MRI systems operation. The wavelength of cylindrical phased arrays at this frequency is very long, of the order of 3 m-5 m in the air. Even in the internal tissues with high dielectric constant the creation of the focal spot of 1 cm in diameter is impossible. Besides, the suggested hyperthermia method requires simultaneous guidance of an RF focused location by an MRI system operation, which is difficult and expensive.

U.S. Pat. No. 10,967,195 to Van Rhoon et al. describes a mechanical arrangement designated for a limited application of a focused microwave radiation for treatment of tumors in the throat without disclosure of the type of radiators used in the patent and methods of control. The patent is limited to a detailed description of a mechanical arrangement for patient convenience.

U.S. Pat. No. 5,097,844 to Turner utilizes a cylindrical antenna array of long dipoles with phase and amplitude controllable sources. The patent utilizes a phase and amplitude control of radiating elements but operates at low frequency. As the author indicates: "It is most useful between 60 to 220 MHz where the penetration characteristics of the body are deeper." Low operating frequency limits the mechanical design to large cylindrical structure surrounding the torso and is not usable in high microwave frequencies where the losses in human tissues are very high.

Figure 3:
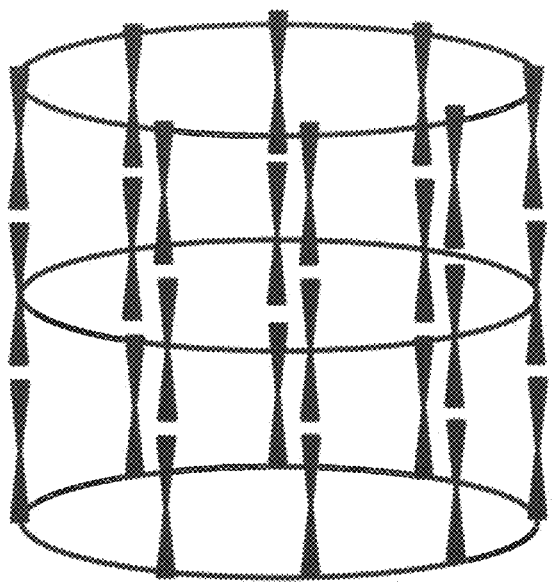

FIG. 3 taken from U.S. Pat. No. 10,737,106 shows a typical construction of the focused array used for a head or torso hyperthermia. Similar comments can be related to U.S. Pat. No. 10,737,106 by the same author, where he substituted a single power source by several amplifiers feeding a sub-array group of three antennas and targeted application to the head tumors treatment.

In conclusion of the survey of existent patents and scientific literature, it can be noticed that there is a definite need for a solution and implementation of the recently discovered phenomenon of SAR for destruction of COVID-19 and applicable for other viral infections treatment.

SUMMARY OF THE INVENTION

Accordingly, it is an object of the present invention to provide a method and an apparatus for treatment of patients with viral infection, which avoid the disadvantages of the known methods and apparatuses in this field, and provide for highly advantageous results.

In keeping with these objectives and with others which will become apparent hereinafter, one feature of the present invention resides in a method of treatment a patient infected with a virus that includes steps of identifying the virus which infected the patient;
  determining an acoustic resonant frequency or frequency bandwidth corresponding to the identified virus;
  identifying a threshold electric field strength $E_{th}$ and Electro-Magnetic (EM) power density $P_{th}$ required for a complete or a partial destruction of the virus in a patient's organ designated for a treatment;
  mapping the patient's organ designated for the treatment using MRI, tomography or another imaging method and using results for programming an antenna array beam forming network (BFN);
  developing a model for the designated for the treatment of an EM wave propagation through anatomical tissue layers using a numerical bioelectromagnetics;
  selecting an NFF broadband antenna array which is best applicable for irradiation of the patient's organ designated for the treatment and having an operating bandwidth wide enough to operate at a single resonant frequency, or simultaneously operate at several separate frequencies, or operating in a continuous frequency sweeping mode over specific frequency band corresponding to a CAV frequency range of the virus, using in an NFF technology at least one microstrip array, horn antennas, linear dipoles and monopoles, spiral antennas, waveguide apertures, Vivaldi arrays, waveguide slot arrays, and other antennas suitable for the treatment of the patient's organ;
  creating a space/time plan of movement of a focal spot for treatment of the infected organ based on information obtained during mapping of the patient's organ;
  creating a software program for phase/amplitude values for steering a focal spot of a selected Near Field Focus antenna array over a full volume or a partial volume of the organ designated for the treatment, and controlling the steering by a digital Beam Forming Network;
  connecting a microwave source or microwave sources operating with operational parameters at a single frequency, or several frequencies, or continuously sweeping over the identified frequency band width and having a sufficient power delivered to radiating elements to achieve the identified threshold field strength and the power density in the focal spot required for a complete or a partial destruction of the identified virus in the patient's organ designated for treatment;
  controlling a temperature of the organ designated for treatment to prevent overheating of surrounding tissues using a microwave radiometer connected to the same irradiating NFF antenna array or to a separate NFF antenna array;
  if two different antenna arrays or different frequencies are used, controlling phase parameters of both receive and transmit antenna arrays in such a way that focal spots from both arrays provide a synchronous 3-D movement inside of the organ under the treatment covering the same area inside of the organ designated for the treatment, and so that when a common Near Field Focus antenna array is used for irradiation (transmit, Tx) functions and for a temperature control (receive, Rx) functions, a condition of a synchronous movement of Tx and Rx focal spot will be satisfied automatically if a same frequency or frequency band is used for Tx and Rx operation; and conducting approximately 15 minutes to one hour treatment sessions to eradicate the virus.

Another feature of the present invention resides in an apparatus for microwave radiation treatment, comprising:
  a microwave power generator or several generators having operating frequency equal or close to microwave frequency at which maximum SRET power has been absorbed by viral pathogen, or capable of radiating variable frequency, or several fixed frequencies covering bandwidth of MRA for viruses with different sizes and mass;

the power of the generator(s) must be equal or above the level sufficient to provide the field strength and power density at the organ under treatment to produce Confined Acoustic Vibrations (CAV) with amplitude above the threshold to cause acoustic mechanical destruction of the virus shell (capsid lyses);

the conformal antenna array that has a gain capable of creating focal spot to irradiate organ under the treatment with said NFF spot having electrical field strength and power density sufficient to cause CAV in the virus with amplitude producing a destructive stress in the virus lipoid capsid;
- conformal antenna array where digital beam-forming is implemented for computerized control of amplitude and phase of radiating elements to create the focused microwave energy spot in the required positions inside of the organ under the treatment using data obtained as a guidance;
- the conformal arrays with radiating elements that are used for treatment of the organs located deep inside of the body (lungs, for example) and may use high EM power, are thermally insulated from the skin by layer of dielectric (so called "coupling bolus") with circulating liquid to minimize rise of the skin temperature caused by high EM power application and protecting nearest fat and muscle tissues; also using said bolus to provide impedance matching to minimize surface reflections from the antenna—body interface by selecting circulating liquid with proper dielectric constant and low microwave loss coefficient (low tanδ);
- the conformal arrays can be used for different organs treatment and require cooling bolus, wherein said arrays are printed on flexible printed circuit board (PC-board) and located inside of the conforming water bolus, wherein antenna array PC-boards and cooling bolus are assembled into elastic support structure in the shape of the vest that snugly fits the patient torso or in the shape of the collar to fit around patient's throat, or in the shape of nose maxilla to irradiate nasal air passage and sinuses area;
- a vest wherein, if the separate irradiating array and radiometer array are selected, they are placed on the opposite sides of the vest, for example: if the irradiating antenna PC-boards are located in part of the vest covering the front (anterior) of the torso, the radiometer antennas will be located at the rear (posterior) part of the vest, or at the torso lateral sides;
- the conformal array in the shape of collar with or without bolus around the neck of the patient with the goal of irradiating virus infected larynges located in this area;
- the array assembly, wherein depending on the results of the previous step the water bolus may or may not be used for treatment procedure; and
- the antenna array assembly in the shape of two NFF arrays with two planar or curved PC-boards assembled as a two-panel assembly with the angle between two planes and the size of the planes is determined by the anatomy of the patient, said assembly positioned in the patient face proximity.

When the method is performed and the apparatus is designed according to the present invention they achieve highly advantageous results for treatment, which will be described further on in detail.

The present invention residing in the new method and apparatus is illustrated in the drawings specified below.

BRIEF DESCRIPTION OF THE DRAWINGS

FIG. 1 is a view showing a prior art intracutaneous ablation antenna with a liquid cooling to preserve surrounding tissues;

FIG. 2 is a view showing an prior art experimental setup for a virus inactivation with vials containing viruses which have been irradiated;

FIG. 3 is a view showing a prior art typical construction of a focused array used for a head or a torso hyperthermia;

FIG. 4 is a view showing a sequence of steps required to implement the method according to the present invention;

FIG. 5 illustrates a method according to the present invention for treatment of human lungs;

FIG. 6 shows an implementation of present invention treatment method of infected lungs with antenna arrays on sides of a patient's torso;

FIG. 7 is a diagram of a first embodiment of the invention with TX and RX separate arrays;

FIG. 8 is a diagram of a second embodiment of the present invention with a separate control and monitoring using the same antenna array;

FIG. 9 is a diagram of a third embodiment of the present invention with a radiometer operating in the same frequency as a radiating system and using the same antenna array;

FIG. 10 shows an apparatus for medical application with individually controlled sub-arrays;

FIG. 11 is a view showing typical lungs location in human body;

FIG. 12 is a view showing an organ model using anatomy of an atlas-based tissue segmentation;

FIG. 13 is a view showing a torso enveloping vest to be applied around a patient's torso for lungs treatment;

FIG. 14 is a block-diagram of an array with digitally controlled phase shifters;

FIG. 15 is a view showing a conformal antenna array for a lung treatment application;

FIG. 16 shows an implementation of a COVID-19 viral treatment using a multiple RF sources;

FIG. 17 shows a calculated diameter of a focal spot as a function of a focal distance from an array plane;

FIG. 18 schematically shows a cross-section of a treatment process of virus—infected lungs using focused EM field;

FIG. 19 is a view showing the anatomy of a treatment area for larynges;

FIG. 20 is a view showing operation of the embodiment for larynges treatment for SARS-Cov-19 virus.

FIG. 21 is a view showing positioning of an antenna array inside a bolus in a front area of a patient's neck;

FIG. 22 is an illustration of an antiviral treatment of a larynx area using microwave radiation therapy;

FIG. 23 is a view illustrating a focal spot control for larynx treatment;

FIG. 24 is a view showing a cross-section of head orifices with areas desirable for irradiation;

FIG. 25 shows a positioning of irradiating arrays on a face of a patient;

FIG. 26 shows a printed circuit board with broad band radiating elements for nasofarinx treatment using present invention; and FIG. 27 shows a setup for treatment of patients' nasal cavities and nasofaringes infected with COVID-19 virus.

DESCRIPTION OF PREFERRED EMBODIMENTS OF THE INVENTION

COVID-2-SARS infecting process takes approximately 10 hours during which the virus makes intracellular virions

[15]. This source also reports the amount of viruses per swab from nasal-pharynges area as up to $10^9$ RNAs/swab and from throat phlegm up to $10^{11}$ RNAs/ml. It is obvious, that even partial weakening of viral load in the body by microwave radiation using SAR for virus destruction will decrease the severity of the disease.

The invention discloses the method and apparatus for noninvasive treatment of patients, who contracted viral infections such as COVID-19, influenza, and other viral diseases, using phenomenon of microwave energy coupling to acoustic energy vibrations inside of the virus capsid, leading to its' lyses and destruction.

The discovery of the possibility of coupling of acoustic resonant vibrations in viruses to the external electromagnetic waves in [3], [4], [5], [6] with frequency equal to virion's acoustic resonance frequency created a possibility of "swinging" the charges in by-polar shell of the virus with electric field amplitude high enough to cause the rupture of virion protein capsid. The SAR method require certain threshold electrical field amplitude. To achieve this goal, the direct application of the microwave energy from external source through antenna, as described in [4] will require prohibitively high power density at the skin surface.

The present application deals with a method using NFF antenna arrays for external delivery of lowest possible EM field by creation of small spot of concentrated energy inside of the organ containing viruses with required power density to destroy the virus. The focal spot is moved inside of the organ in a controlled way to irradiate full volume of the organ. For COVID-19 and other SARS viruses treatment it can be lungs or larynges, or nasal passages. The safety of the patient is ensured by monitoring of the tissue temperature in the vicinity of the irradiated spot by passive microwave radiometer connected to the irradiating array or separate NFF antenna array operating at lower frequency for better body penetration in which focal spot movement is synchronized with movement of the irradiating spot. Another advantage of the proposed method is that it teaches practical implementation of the simultaneous application of multiple frequencies or broad band frequency continuous sweeping for destruction of Covid-19 viruses with range of different sizes and/or mass originally suggested in [6].

The present application exploits extreme flexibility of NFF antenna arrays to control the side-lobe level, shape the −3 dB focal spot, implement multifocus patterns, and electronically stir the focal point in 3-D space.

The proposed treatment procedure for the NFF antenna array used for SARS virus infected patient is as follows:
1. After clarifying the type of the virus that infected the patient, determine the exact dimensions of the patient's organ under the treatment using X-ray or MRI or other methods. Use measured parameters of the organ in the program for control of the movement of irradiating focal spot.
2. Estimate electrical field amplitude and microwave power density required for virions rapture. If this is the case of COVID-19 infection, the reported value of $P_{th}=14$ W/m$^2$ is acceptable value for 100% eradication over 15 minutes session. $P_{th}=1.5$ W/m$^2$ allowed for 38% of virus deactivation [3], [4], [6].
3. Select the frequency of the microwave source equal to acoustic resonant frequency of the virus. For SARS-CoV-2 viral infection typical frequency band is 8.5-17 GHz [4], [6].
4. Estimate propagation losses from the skin surface to the center of the organ. Create theoretical model of multilayer EM wave propagation from NFF antenna array positioned outside of the body through layers of skin, fat, muscle, and others to the organ to be irradiated. For this task multidisciplinary optimization software (MDO) such as VSimEM, XFdtd, and others can be used. The detailed description of the method using Finite Difference Time Domain (FDTD) is given in [23].
5. Select microwave matching of propagation medias between antenna array and human body to minimize reflections (this matching layer called bolus). Using circulating liquid dielectric, the bolus is also can be used for cooling of the nearest layers of the skin and fat from temperature rise caused by irradiating array. The results of multiple experiments and studies of the dielectric constant of this matching layer shows that the minimum reflections were achieved by the layer having thickness close to ¼ of the operating wavelength and dielectric constant in the range of 5 to 10, depending on the irradiated area of the body. In some applications, such as nasal cavities or larynges, the bolus may not be needed.
6. Select the appropriate microstrip conformal NFF array(s) with focal points capable to irradiate the entire organ. Preprogram the beam-former processor for 3-D focal spot movement using size/location information of the organ obtained in the steps 1 and 4.
7. Similarly to step 6, select location and parameters of the passive temperature monitoring array and synchronize the movement of focal spot of the radiometer array with movement of the irradiating focal spot.

Figure 4:
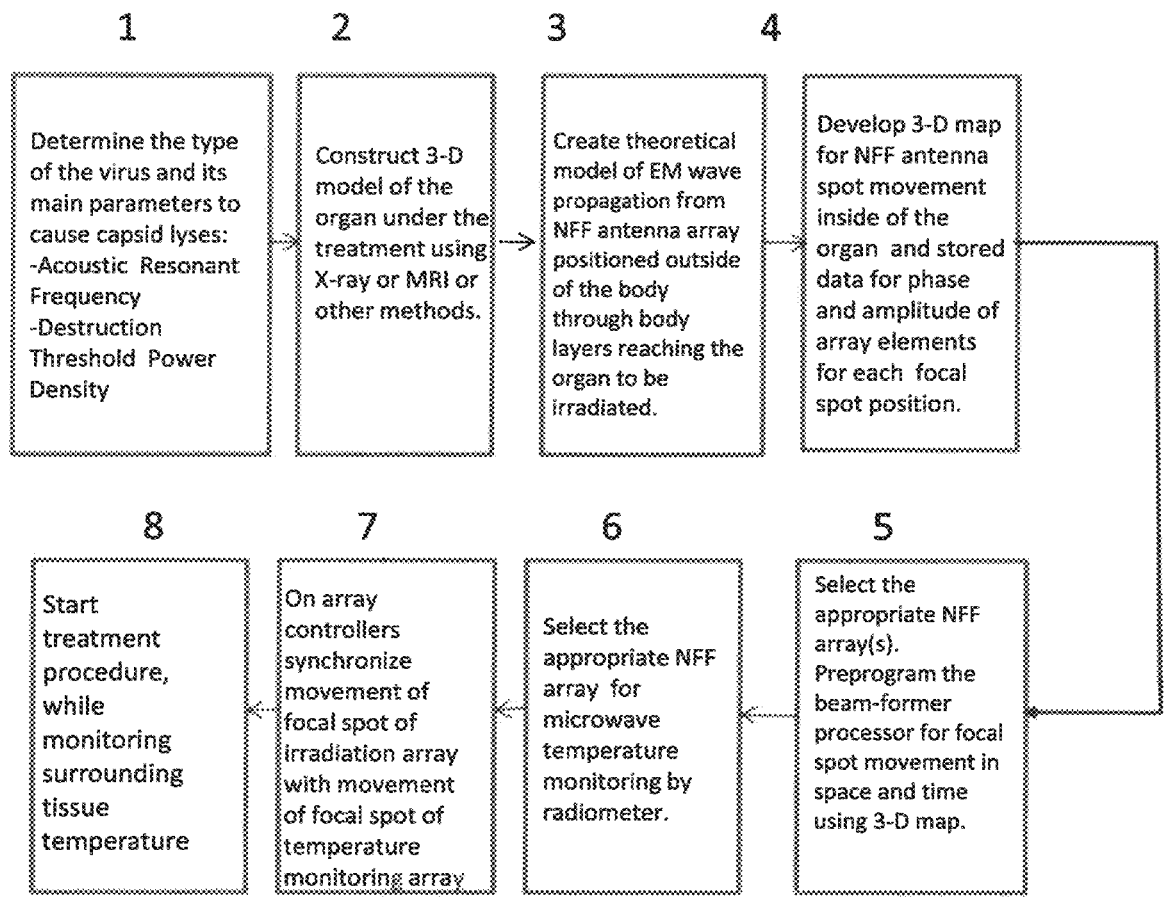

FIG. 4 shows the sequence of steps required in order to implement the described method of the SARS treatment.

Figure 5:
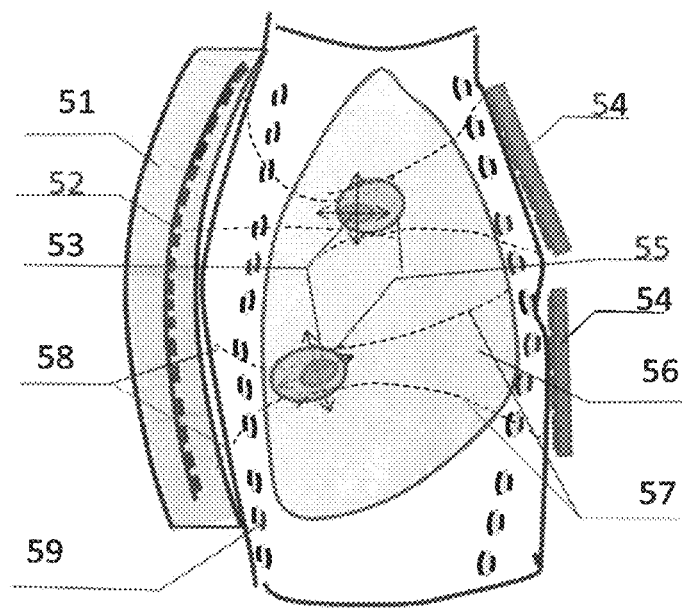

FIG. 5 illustrates the described method applied for the treatment of human lungs. In FIG. 5 NFF arrays 52 (conformal microstrip version is shown) are designed according to step 6 (block 5 in FIG. 4) to destroy SARS infection in the patient's lungs 56. These irradiating NFF arrays shall operate in the virion's acoustic resonance microwave band and, as shown, can be located inside of the cooling-matching bolus 51 closely attached to the patient's chest, or back, or side of the torso, using specially designed vest. Array creates high field intensity small focal spots 53 capable of moving inside of the lung volume in a controlled way. FIG. 5 also shows microwave field distribution 58 creating required focal spot with high intensity. The array size and number of radiating elements is selected in such a way that its focal spot(s) movement can cover full volume of organ under the treatment (lungs are shown). Single large array is shown capable of creating a single or multiple focal spots. Similarly, several smaller arrays independently controlled can be used. Ribs cartilage 59 of the human torso are also shown. If the full depth of the organ cannot be reached from the single position of the bolus, anterior for example, the location of the bolus with irradiating array can be switched with receive radiometer antennas 54 to posterior location and procedure will be repeated.

This temperature monitoring method implies lower frequency NFF phased array located on the opposite side of the body in reference to the irradiating array and having synchronized movement of the focal spot in such a way that spots of both arrays cover the same volume with the temperature array receiving spot located where the maximum EM energy absorption happens, usually in the area with the maximum microwave propagation loss. Arrays 54 shown in FIG. 5 are located on the opposite site of the body and connected to microwave radiometer for temperature monitoring. The operating frequency of radiometer array is selected considering the maximum absorption of microwave energy in the human tissue. For example, it can be 2.45 GHz, which is used for typical biological objects because it is close to the resonant frequency of water molecules. The size of the focal spot is not critical, as long as it engulfs the irradiating "hot spot".

Radiometer conformal receiving arrays can be positioned on the opposite side of the patient's body to avoid obstruction for irradiating arrays. Two separate antenna arrays for temperature monitoring are shown in FIG. 5. This antenna array can be single multi-focal conformal array similar to irradiating array 52 but designed for lower operating frequency. FIG. 5 also demonstrates close monitoring of the temperature in irradiating spots 53 by synchronizing the patterns' location and focal spots 55 movement controlled by temperature monitoring receiving antennas 54. Alternatively, based on antenna duality principle, the radiometer, can be connected to the same antenna array as irradiating source(s), and the temperature sensing around irradiating area will be achieved automatically. Obviously, in this case radiometer must operate in the frequency band covered by irradiating antennas.

Figure 6:
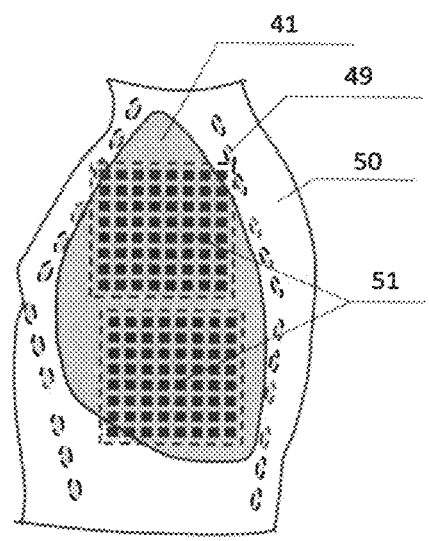

FIG. 6 shows implementation of this treatment method of infected lungs by positioning antenna arrays on the sides of the patient's torso 60 (lateral position of array). Two separate independently controlled arrays 62 are shown. Lateral view of the lung marked 61 and cartilages marked 63. Also, a single larger array with bolus (similar to 51, 52 in FIG. 5) with multi-focal capabilities can be used, depending on the size of the organ under the treatment and condition of the patient. Temperature monitoring antennas similar to 54 (FIG. 5) are located on the opposite, anterior or posterior side of the torso, or radiometer can be connected to the irradiating arrays.

Figure 7:
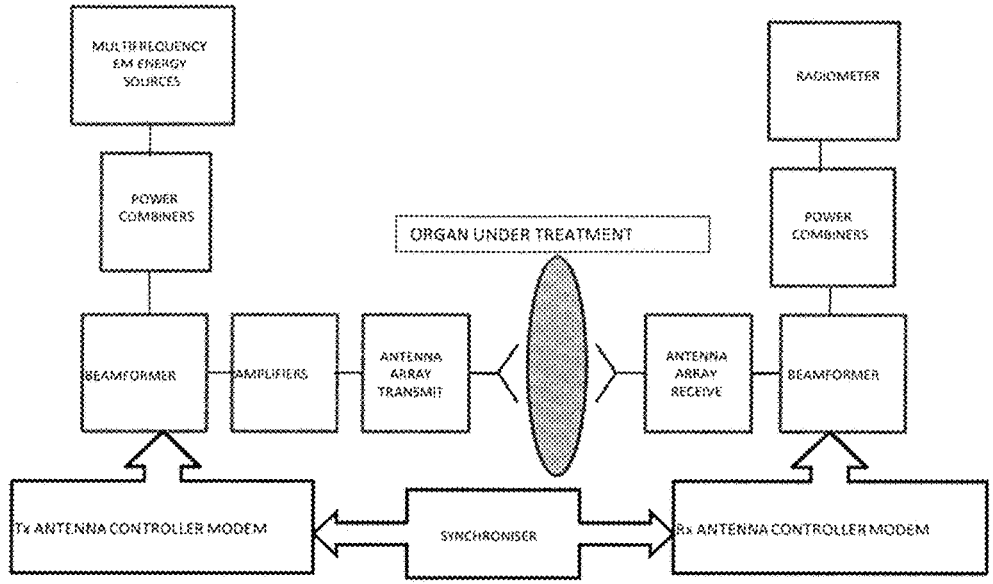

A block diagram of the first embodiment of the method described above with TX and Rx separate arrays is shown in FIG. 7.

This embodiment allows for a maximum flexibility because the position of the receive and transmit arrays' focal spots can be independently controlled. As can be seen from the diagram in FIG. 7 the set of sources with selected microwave frequencies is connected to broadband microwave combiner-divider network that provides a full set of frequencies to each baseband beamformer, which controls amplitude and phase for corresponding sub-array. Low power outputs from beamformers are connected to high power broadband amplifiers that provide required power for EM energy enough to penetrate external tissues for irradiation covering full volume of the organ with the power enough to cause high amplitude acoustic resonance in virions that leads to their destruction.

Figure 8:
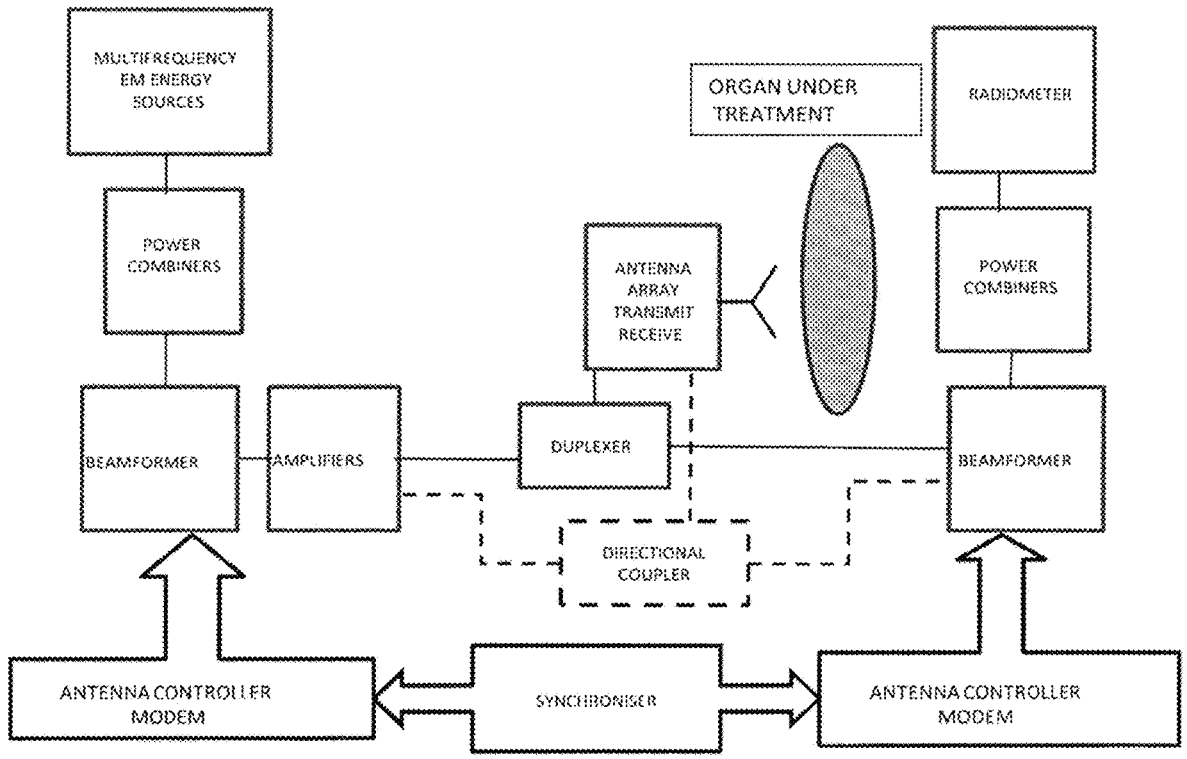

The second embodiment of the method of the invention with a temperature control and monitoring is shown in FIG. 8. In this embodiment the system is taking advantage of a broadband NFF capability and possible optimal frequency difference between a receiving band for a radiometer and a transmitting band for irradiation of the organ under the treatment. Low loss reactive frequency duplexers are used for separation of transmit and receive paths that significantly simplifies the system design and implementation allowing for use a single antenna array for transmit and receive signals. To implement this solution, receive (Rx)-transmit (Tx) elements in the NFF array must support both transmit and receive selected bands. This approach still realizes possibility of independent control of the NFF array focus spot by using separate beamformers for receiver frequencies, but does not require an additional receiving array for a temperature control. This embodiment allows for an optimal operating frequency selection for receiver-radiometer as long as it can be supported by common antenna array elements. Alternatively, the duplexer is substituted by a directional coupler shown by dotted lines in FIG. 8. In this embodiment the radiometer can still operate at any frequency supported by the array element, but at the cost of losing some sensitivity because of the coupling losses.

Figure 9:
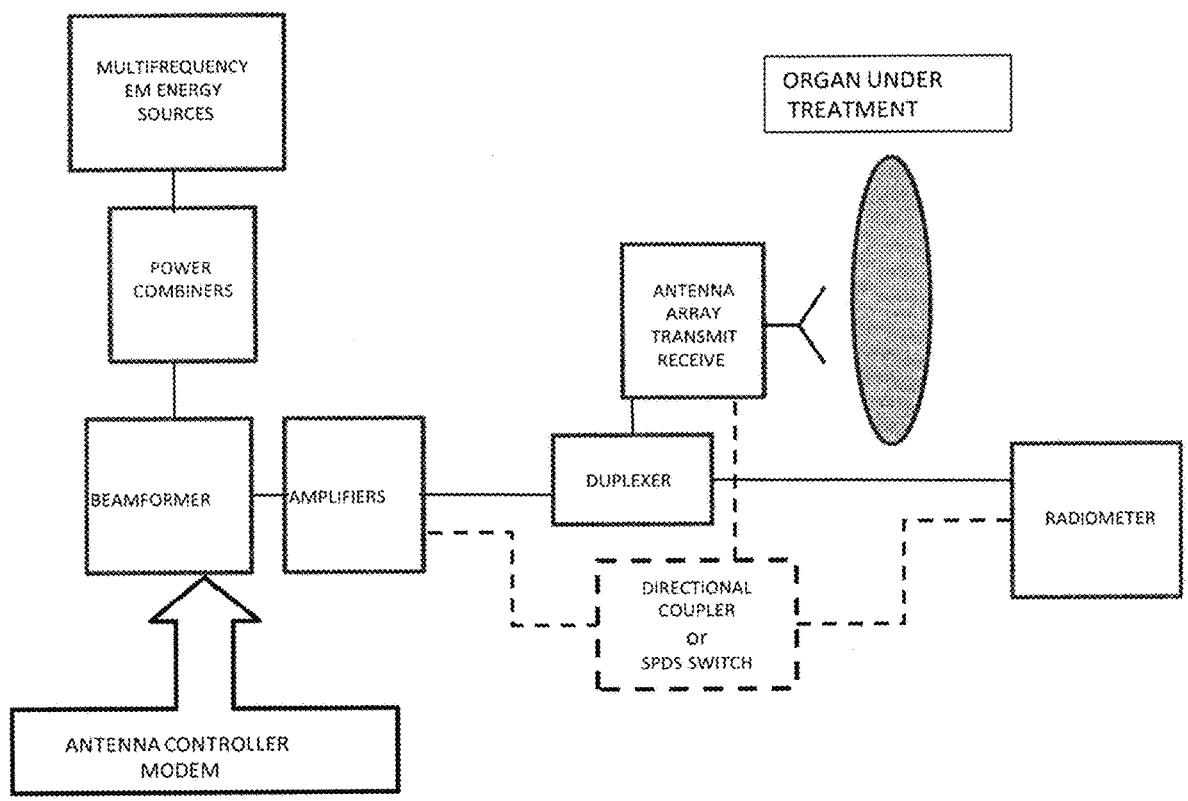

The third embodiment of the system is shown in FIG. 9. A block diagram in FIG. 9 shows the simplest embodiment for a viral patients treatment, in which a radiometer operates in the same frequency band as an irradiating system and receives a signal from the same focal spot controlled by a common antenna array beam-former. For this embodiment the usage of only one NFF array with one set of BF controllers significantly simplifies the system at the cost of independent Tx/Rx focal spot controls. A receive signal can be diverted from a transmit path using a duplexer, a directional coupler, a SPDS switch or any other duplexing means known in the microwave industry.

Figure 10:
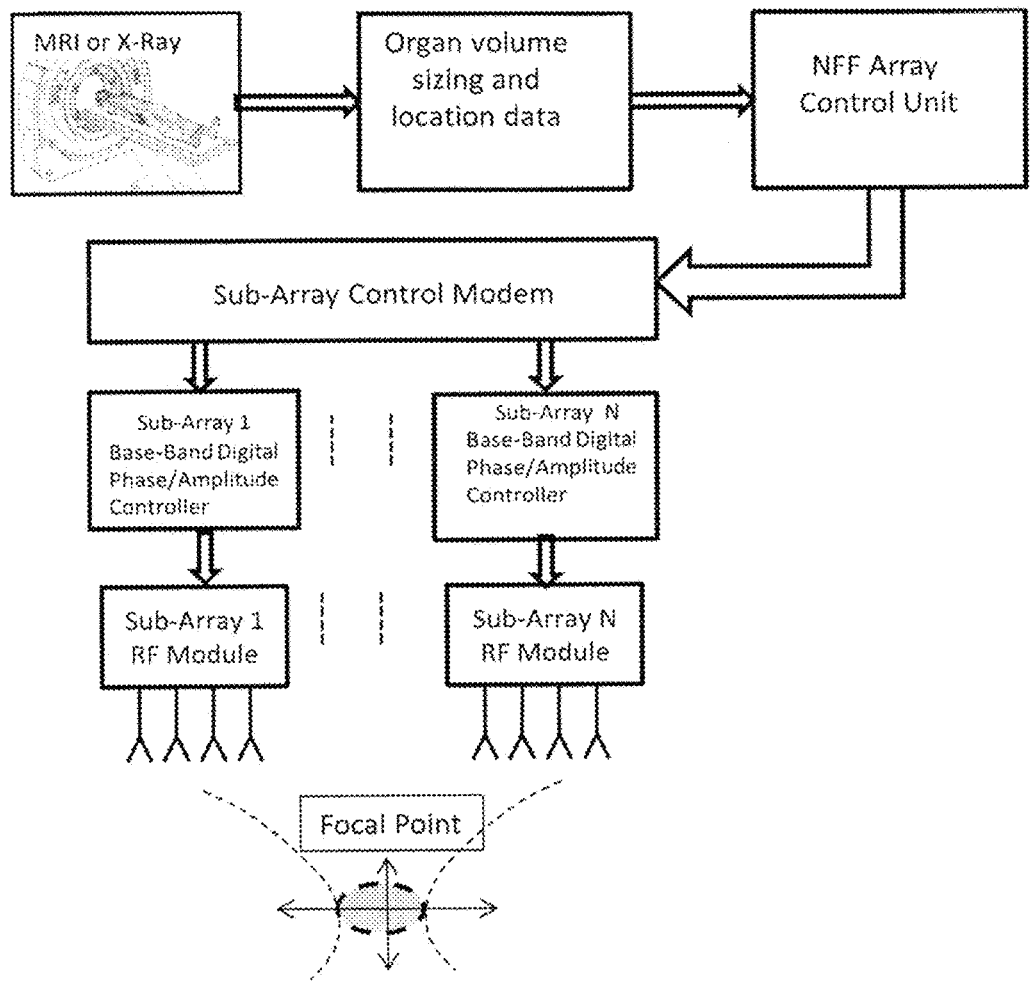

FIG. 10 shows a diagram of the signal processing of the system described in this patent application. After determination of an organ under the treatment physical sizing, volume, and other parameters using MRI or X-Ray or other methods, the data is inputted into the software for creating a propagation model for a specific Acoustic Resonant Frequency of the infecting virus using known methods described, for example, in [23] and [35]. As discussed above, the propagation models play a very important role in this method of viral infection treatment. In order to properly utilize this method, EM propagation models of the path through the tissues to the organ can be simulated on CST Microwave Studio (full Wave Microwave Simulator) by using MRI data of the patient. The models can be derived from a series of T1-weighted magnetic resonance images (MRI) of patients and have 0.5×0.5×0.5 mm resolution [35]. The data is first processed in Matlab to construct a propagation matrix. The matrix is then used to generate a model in CST. Then the propagation data is mapped onto the physical boundaries of the organ obtained from MRI or X-ray scans and entered into NFF Array Focal Position and Time Control Software, where the values for amplitude and phase of EM wave are calculated for each desirable position of the focal spot in the organ under the treatment as well as time intervals for each focus position according to the treatment plan.

FIG. 10 indicates "sub-arrays" for a focal spot control, which typically consist of several radiating elements operating at the same phase and amplitude. This approach can be used for a large organ treatment, such as lungs. For a smaller organ treatment such as larynges or/and nasal cavities, radiating arrays may use a phase and an amplitude control for a single radiating element. In all embodiments the BFN can be realized by different methods. For example, it can use a baseband digital control for the phase in each sub-array and the variable gain power amplifiers for an amplitude control. Similarly, the amplitude control can be realized in a baseband module, keeping power amplifiers at a constant gain. Another approach for BFN realization is to use a switched beam approach for positioning the spot at fixed locations in the organ or simultaneous creation of multisport irradiation of the organ. This circuit is realized by using Butler Matrix implementing fast Fourier transform algorithm. For this beam a control method feeding Butler Matrix can be used with four, eight, and up to sixteen focal spot positions identified in advance during the treatment planning in step 4 (FIG. 4). The RF inputs to the matrix can be switched to irradiate different spots identified in the treatment plan or to realize a simultaneous multisport irradiation. Analysis provided in calculates Discreet Fourier Transform (DFT) terms that result in a set of linear phases to excite the array for directional beams, which are mutually orthogonal to each other. One of the perspective applications of Butler Matrix BFNs is the use of simultaneous feeding of all N input ports with irradiating power to create simultaneous N focal spots in the organ under the treatment, which may simplify the control network and minimize the treatment procedure time.

FIG. 10 shows the most versatile approach applicable for medical applications where each sub-array individually controlled by its own Baseband Phase and Amplitude Controllers, which in turn receive commands from BFN Modem (only Tx part of the setup is shown). Individual sub-array base-band controllers contain baseband digitizing network, mixers, and amplifiers that provide preprogrammed values for phase and amplitude, which is identical for each element of sub-array. The last in the chain stand RF-modules that contain power dividers-combiners, power amplifiers, and antenna radiating elements. FIG. 10 also demonstrates a focal point of concentrated EM field created by sub-arrays radiating properly phased EM waves to be positioned and moved around inside of the infected organ.

An apparatus of the invention for a lungs treatment will be now described in detail. The lungs occupy most of the volume inside of the rib cage (thorax) and, in case of the SARS infection, can be a major source of the new virion creation accompanied with rapidly worsening patient condition. It has to be noticed that the goal of this treatment is not a thermal ablation in the irradiated organ, like it is done in a hyperthermia tumor treatment, but a delivery of a lower power microwave radiation for virus destruction in the organ. Therefore, many other technical solutions may be implemented that can produce controlled focused microwave radiation at different parts of the infected organ.

Figure 11:
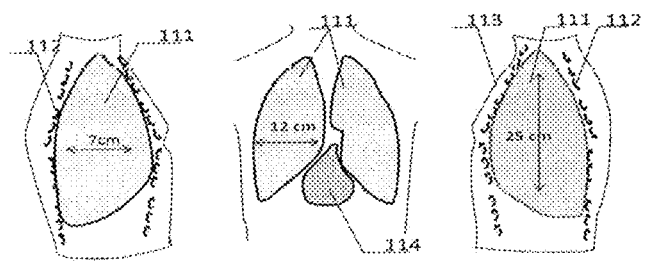

In FIG. 11 the lungs 111 are located between ribs and a ribs cartilage 112. A skin surface 113 and a heart 114 are also indicated. The dimensions shown in FIG. 11 are typical for an adult male and used here as a design example. Actual implementation will require individual scanned data for each patient. One side of the lung can be approximated as a voluminous structure with an oval or elliptical shape having a vertical average size of 25 cm and a horizontal size of 12 cm with the depth at the central axis of 7 cm. From the analysis discussed earlier it is clear that for the treatment of such organ as lungs, the implementation of conformal planar array or arrays capable of covering most of the lung volume with controlled movable focal spot or multiple spots is required.

In order to irradiate lungs with microwave energy with a level high enough to destroy SARS virions, the patient is subjected to the focused microwave beam which intensifies the energy density at the focal spot 100 times (20 dB) compared to non-directional source [14]. The focal spot or multiple spots has to be moved in 3D direction covering most of the lung volume in order to be effective in virus destruction. Irradiation from one side (back or posterior side, for example) of the lung will require the maximum focal distance from the surface of the rib cage approximately 3.5 cm or ½ of the lung depth. After completing the treatment from the posterior side, the treatment from the front (anterior) side can be provided and positions of Tx and Rx arrays (if used) can be switched (FIG. 5). Alternatively, lungs can be irradiated from sides (lateral position of arrays), if the anterior location is impossible or obstructed (see FIG. 6).

Following the plan described above and listed in FIG. 4, as the first step we assumed that the adult male patient is infected by virion CoV-2-SARS type. Currently known COVID virion physical parameters are shown in Table 2.

TABLE 2

| Virion | SARS Acoustic Resonance Frequency, GHz [3] | Required Power Density for Complete Eradication, W/m² [6] | Required Power Density for 38% Eradication, W/m² [3] |
| --- | --- | --- | --- |
| CoV-2-SARS | 6.5-9.5-10.5 | 14.5 | 1.5 |

There is a wide range of frequencies that can cause Structure Acoustic destruction of CoV-2-SARS virus (8.5 GHz-17 GHz, [6]). In [6] also was suggested to sweep irradiating frequency to cause the faster lyses of capsid of viruses with different sizes and mass, and, therefore, different Acoustic Resonance frequencies. In the present invention four separate frequencies or swiping over the smaller frequency band located at the lower end of the range are suggested (Table 2). The reason for that is the variation of the frequency band +/−20% will cause insignificant changes in the position and size of the focal spot, which simplifies the control algorithm. It is important to note, that during the frequency sensitivity study in [3], authors observed shallow resonance in the inactivation ratio over the bandwidth of 35% with the inactivation ratio of virions more than 80% with more pronounced effect at the lower side of the resonance curve. Operating at the lower part of the Acoustic Resonance Frequency band (Table 2) will require less radiating power because of the smaller losses in a human tissue at lower frequencies. Using data obtained in the second step, the treatment plan and positions of the focal spot for 3-D exposure of the patient's organ under the treatment has been recorded and the limiting borders of lungs irradiation have been determined.

Figure 12:
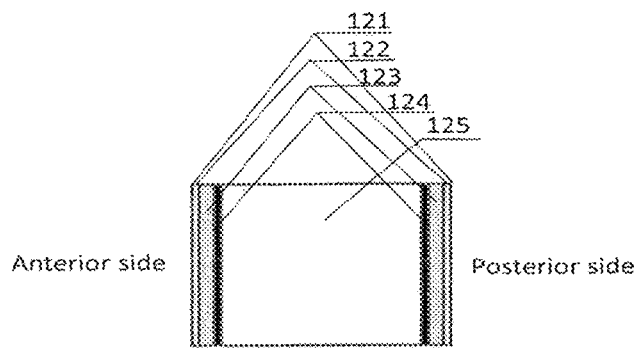

Losses in human body depend on electrical properties of the layers of human tissue through which the desired microwave energy has to pass under treatment by a microwave irradiation. Some EM parameters of human tissue layers under consideration is shown in FIG. 12. Actual sizes of the organ are specific to individual patients and must be obtained from MRI or X-ray scans. The procedure starts with a CT scan typically used for a radiotherapy treatment planning. From that scan the 3D patient specific organ model is created using the anatomy atlas-based segmentation described in [40].

In FIG. 12 outer layers 121 is skin, a layer 122 is fat, a layer 123 is muscle, a layer 124 is ribs cartilage. The lungs volume is shown as a layer 125. For a specific patient all information on the layer thickness was obtained in step 1 of the proposed method. For this exemplarily design a typical information for an adult human is used from the source [37].

The EM wave propagation studies through human tissues show that X and Ku bands microwave frequencies will experience very high losses. The International Commission on Non-Ionizing Radiation Protection (ICNIRP) stipulated the safe microwave power density within 200 W/m². In order to limit an input microwave power to which the skin surface will be exposed below 200 w/m², the maximum value of loss at selected frequencies has to be properly calculated for the organ under the treatment. In order to overcome significant losses experienced by EM beam propagating through different layers to reach the organ with required power density, the applied power density at the surface of the skin must be significantly higher than the safety limit. In order to overcome this problem and protect the patient from overheating by microwave energy the device called "bolus" has been developed and used for a cancer patient treatment [41]. Using a local cooling effect created by the bolus the order of magnitude higher power density can be applied [39]. In [45] the method of treatment of neck tumors using the bolus for cooling of the surface tissues has been described. The applied power was reaching 1000 W in that study.

Figure 13:
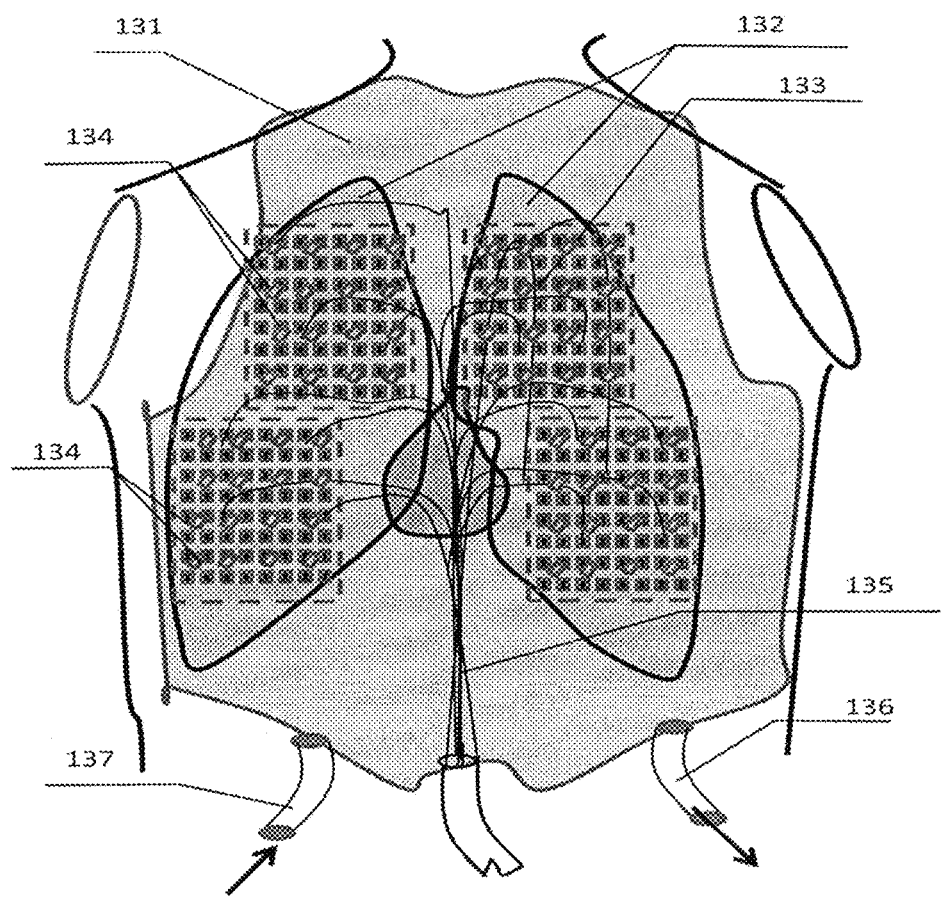

Table 3 demonstrates the effect of high dielectric constant of human lungs on the wavelength and focal spot diameter at selected operating frequencies. As was mentioned in [6], to destroy viruses with different size and mass, the most prudent way to fight COVID infection will be a simultaneous radiation at several microwave frequencies. In this embodiment frequencies have been selected based on results of investigation in [3], where it was shown that inactivation efficiency did not deteriorate significantly up to the lowest frequency 6.5 GHz. At this frequency more than 70% of the virus was inactivated after 15 minutes exposure. The highest operating frequency of the embodiment was selected based on a reasonable penetration of the microwave beam into the lungs volume and implementing a cooling bolus to protect the outermost tissues. Using a deionized water a cooling bolus tightly applied to the body surface, and assuming power density at the focal spot has to be 3 times or more above the virus destruction threshold power, the maximum propagation loss can be calculated. Calculations for the bolus operating parameters are provided in with the recommended water temperature of 30 C for deeper EM energy tissue penetrations. The desired range of exterior skin temperature must be kept in 40-42° C. or below pain threshold. The total power was selected from experimental results to obtain maximum temperature of 40° C. in healthy tissues using a typical bolus for cooling and matching. The bolus assembly containing the conformal microstrip arrays for this apparatus embodiment is shown in FIG. 13.

For convenience of the tight enveloping around the torso for lungs treatment the bolus 131 has a shape of a vest made of materials available in the industry and used for the bolus manufacturing elsewhere [39]. In FIG. 13 the imbedded microwave arrays 133 are positioned opposite the lungs 132. RF cables from watertight sub-array connections 134 are collected into cable assembly 135 with means to exiting out to BFN (FIG. 10). Hose connections 137 (inlet) and 136 (outlet) provide a cooling liquid circulation to cool the body surface under the treatment. From [38] follows that an experimentally established mean heat transfer coefficient for the water bolus has a typical range of 59 to 520 W/m²/K, [39]. The established skin and superficial tissues safe temperature has to be kept around 40° C. with a water temperature in the bolus in the range of 30-35° C. The cooling liquid can be a de-ionized water with a circulating volume 450/L/hr.

Four frequencies that fall in the COVID-19 virion SAR band have been selected for this embodiment. It can be reasonably assumed that the array applied power for each frequency will be 100 W. Results calculated on the premise that for a typical short focused NFF antenna array the focal spot has a diameter of $1\lambda_g$ are shown in Table 3. Several single frequency oscillators can be substituted by a single slow sweeping or stepping oscillator capable of operating in SAR frequency range.

TABLE 3

| Frequency, GHz | 6.5 | 8.5 | 9.5 | 10.5 |
|---|---|---|---|---|
| $\varepsilon_r$ lungs | 18 | 17 | 16.4 | 15.90 |
| $\lambda_g$ in lung, cm | 1.09 | 0.86 | 0.78 | 0.72 |
| d spot, $\lambda_g$ | 1 | 1 | 1 | 1 |
| Power Density Required, w/m2 | 5 | 5 | 5 | 5 |
| Power of the external source, w | 100 | 100 | 100 | 100 |
| Allowed Propagation Loss, dB | 73.33 | 75.41 | 76.22 | 76.96 |

In Table 3 Allowed Propagation Loss was calculated as a ratio between a required power density at the focal spot for virus destruction and an applied safe power density using bolus. One can notice that the actual focal spot diameter is approximately the same for all frequencies because of the frequency dependence of lungs' relative dielectric constant $\varepsilon_r$. This phenomenon simplifies a control of a focal spot for a broad band frequency operation.

The third step requires a creation of a space-time control movement of the focal spot of the array. For general requirements for the array parameters, the specific to the organ propagation path and losses should be analyzed. For the lungs treatment the detailed propagation analysis through the human body has been done in [22]. The charts published in this work can be used for different operating frequencies applied for the treatment.

By interpolating these charts for selected operating frequencies for this apparatus embodiment, Table 4 with information for a lungs penetration depth for each frequency has been calculated.

Using charts published in for calculation the EM wave propagation losses for different tissue layers the penetration depth of the focal spot with power density of 5 W/m², which is more than three times of the minimum threshold power density 1.5 W/m², can be found from Table 4.

TABLE 4

| | | Frequency, GHz | | | | | | | |
|---|---|---|---|---|---|---|---|---|---|
| | | 6.5 | | 7.5 | | 8.5 | | 9.5 | |
| Tissue | Thicknss, cm | Loss, dB/cm | Loss in Tissue, dB | Loss, dB/cm | Loss in Tissue, dB | Loss, dB/cm | Loss in Tissue, dB | Loss, dB/cm | Loss in Tissue, dB |
| Skin | 0.3 | 3 | 1 | 5 | 2 | 6 | 1.8 | 7 | 2.1 |
| Fat | 0.2 | 3 | 0.6 | 5 | 1 | 6 | 1.2 | 7 | 1.4 |
| Muscle | 1.5 | 10 | 15 | 13 | 19.5 | 15 | 22.5 | 17 | 25.5 |
| Cartilage | 0.6 | 13 | 8 | 17 | 10.2 | 19 | 11.4 | 23 | 13.8 |
| Lungs | | 12 | | 16 | | 20 | | 23 | |
| Propagation Loss to Lungs | | | 24 | | 33 | | 37 | | 43 |

TABLE 4-continued

| | | Frequency, GHz | | | | | | | |
|---|---|---|---|---|---|---|---|---|---|
| | | 6.5 | | 7.5 | | 8.5 | | 9.5 | |
| Tissue | Thicknss, cm | Loss, dB/cm | Loss in Tissue, dB | Loss, dB/cm | Loss in Tissue, dB | Loss, dB/cm | Loss in Tissue, dB | Loss, dB/cm | Loss in Tissue, dB |
| Allowed loss in Lungs | | | 49 | | 42 | | 39 | | 33 |
| Maximum Lung EM Energy Penetration, cm | | | 4.1 | | 2.6 | | 1.9 | | 1.5 |

The calculations in Table 4 have been made for the applied power at array of 100 W per carrier. The penetration depth values are typical and must be calculated for each individual patient considering anatomy of his organ, size of array, and used frequencies for treatment. Table 4 demonstrates that using the microstrip NFF antenna array with practically realizable power at the source, the multi-frequency irradiation method of COVID-19 lungs treatment is possible with a significant penetration of a microwave energy into the lungs volume with a sufficient power density level to cause Confined Acoustic Vibrations (CAV) in infectious viruses and, as a result, their destruction. As it follows from safety irradiating power limitations, with properly designed bolus the simultaneous irradiation of lungs with several frequencies from anterior and posterior positions of NFF arrays can achieve a full lungs volume treatment using the proposed embodiment.

It is important to note that EM energy penetration in lungs significantly depends on the patient's anatomy and in some cases the losses in tissues may be very high, prohibiting irradiation of lungs at higher frequencies because of the safe power limitations for the specific bolus design. In this case a longer time irradiation at lower frequencies may be implemented to achieve a desirable result and keep the power density at the irradiation spot above $P_{th}$.

In the next step of this embodiment design the actual antenna array approach is selected. As it was discussed earlier, a conformal printed circuit array is the most suitable antenna solution. Conformal printed circuit arrays with a near field focus allow significant 3-dimentional freedom in positioning of the focal spot at the desirable location simply by changing the phase relationship between radiating elements. It can be seen from equation (4) that describes a phase conjugate approach to create a focal point where radiating fields from all elements will be added in-phase:

$$\phi_{mn} = 2\pi/\lambda * \|R_{focal} - R_{mn}\|_2, \quad (4)$$

wherein $\phi_{mn}$ is the relative phase between the radiating elements,
$\lambda$ is the free-space wavelength, and
$\|\cdot\|_2$ stands for the Euclidean distance.

From (4) it can be seen that by changing the phase shift between the elements of the array, the position of the focal spot can be changed in a three-dimensional space. There are multiple sources discussing different methods of NFF antenna array design including an advanced computer based electromagnetic field modeling [14], [15],[16]. The method described below serves as an example of possible practical solution for this embodiment implementation.

FIG. 14 shows the proposed block-diagram of the array with digitally controlled phase shifters that is capable of controlling a position of the focus in the required locations inside of the irradiated organ. NFF antenna array with a large number or elementary radiators allows for a significant flexibility for a spatially controlled focal point with an electrical field amplitude sufficient to cause a Structure Acoustic Resonance to destroy the virion's capsid and completely inactivate it in the irradiating zone. Beamformers control the radiation pattern through the constructive and destructive superposition of signals from the different antenna elements. With digital beam-forming (DBF), the beam-forming is performed digitally at a baseband, requiring one beam-former and RF Front End (RFFE) that includes a high power amplifier, for each sub-array. Offering a high degree of control, DBF is considered the best and the most flexible approach for receiving and transmitting wideband signals and, more importantly, for variable beam position applications. The digital implementation has greater flexibility for phase and amplitude control in each element allowing controlled location change of the focal spot inside of the organ according to the preprogrammed algorithm. Digitally controlled variable phase shifters ($\phi$) and amplitude set all needed parameters for each position of the focal spot inside of the organ. The example of one of the most advanced methods of NFF antenna arrays is described in [36], where the very quick adaptation of the radiated field and weight coefficients for the array beam-formers have been calculated using neural networks.

To avoid a beam "squint" effect for wide band applications, which exists for narrow band transmission line phase shifters, the time delay solution is used for this embodiment for the control of the phase in DBF. The ability of DBF to compensate for a phase and time delay of different array elements allows significant independence of the antenna geometry from desired performance, making many different configurations feasible, including a practically frequency independent convenient physical shape conformal array. Contemporary ASIC modules [23] contain all necessary digital circuitry including A/D and D/A converters that needed for a computer controlled beam synthesis.

In order to fully realize the benefits of a multi-frequency organ irradiation, the elementary radiating elements must be broadband with low VSWR over the operating band. There are several classes of antennas operating over octave or even wider bandwidth. In this embodiment a bow-tie radiator type is selected because of its planar geometry and easy adaptability for a microstrip design [27]. In FIG. 15 the conformal antenna array suggested for a lung treatment application is shown with 4×4 sub-arrays 152, where each sub-array consists of four wideband elementary microstrip antennas 151. Bow-tie balanced microstrip radiators are shown as an example. The feeding structure using microstrip baluns is described in [27] and [44].

Figure 16:
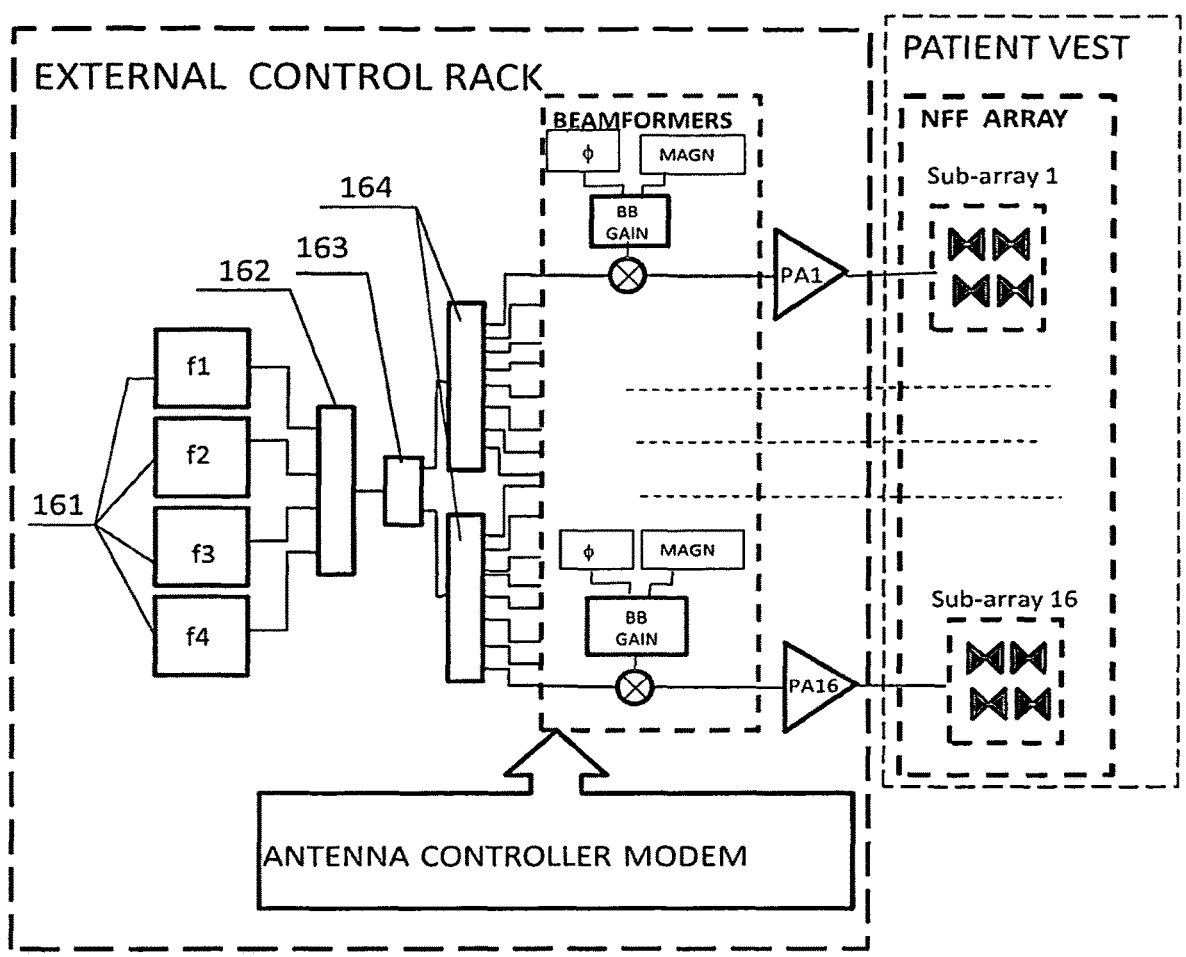

In FIG. 16 the implementation of COVID-19 viral treatment using multiple RF sources (four are shown) is demonstrated. Each low power source with frequencies f1-f4 (161) is connected to a microwave combiner 162, which, in turn, serves as an input to a microwave power divider 163.

If several single frequency oscillators are substituted by a single slow sweeping or stepping oscillator capable of operating in selected frequency range, the power combiner can be omitted and a sweep oscillator will be connected directly to power divider 163. At two outputs of this power divider all four frequencies are present.

By connecting these outputs to two eight-way power dividers 164 one can create a broadband input network for sixteen sub-arrays. Two big dotted line module groups indicate the equipment assembled in an external control rack marked EXTERNAL CONTROL RACK, which is connected to the patient module marked PATIENT VEST with a water bolus and microwave NFF antenna arrays via cable assemblies.

For this embodiment parameters of the focused beams of an 8×8 NFF array of 6.5 GHz-10.5 GHz broad band butterfly patches are shown in Table 5. Outline dimensions of one NFF array is approximately 12 cm×12 cm. Four such array assembled into a vest wearing by a patient can provide EM energy for both lungs from the front or from the back sides of the body.

TABLE 5

| Frequency, GHz | 6.5 | 7.5 | 8.5 | 9.5 | 10.50 |
|---|---|---|---|---|---|
| $\lambda o$, cm | 4.6 | 4.0 | 3.5 | 3.2 | 2.9 |
| $\lambda g$, lungs | 2.06 | 1.79 | 1.58 | 1.41 | 1.28 |
| Elements Space, $\lambda g$ | 0.56 | 0.64 | 0.73 | 0.81 | 0.90 |
| D, space sub-array, cm | 2.30 | 2.30 | 2.30 | 2.30 | 2.30 |

Figure 17:
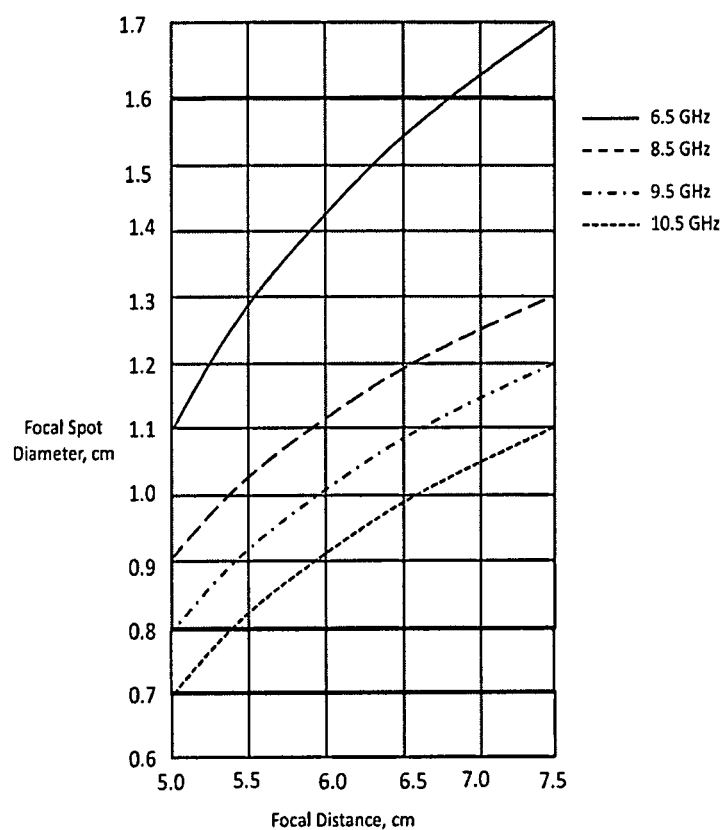

A bolus dielectric constant for the parameters shown in the Table 5, is $\varepsilon=5$. The bolus serves not only for a skin cooling purpose, but also to provide a matching layer between an antenna array and human tissues. As can be expected, because of the broadband properties of the radiating structure, the geometrical parameters of the focal spot will be frequency dependent. A calculated diameter of the focal spot as a function of the focal distance from the array plane is shown in FIG. 17. The chart is plotted assuming approximately 2.0 cm internal bolus space between the array, shown in FIG. 15, and a skin surface.

Figure 18:
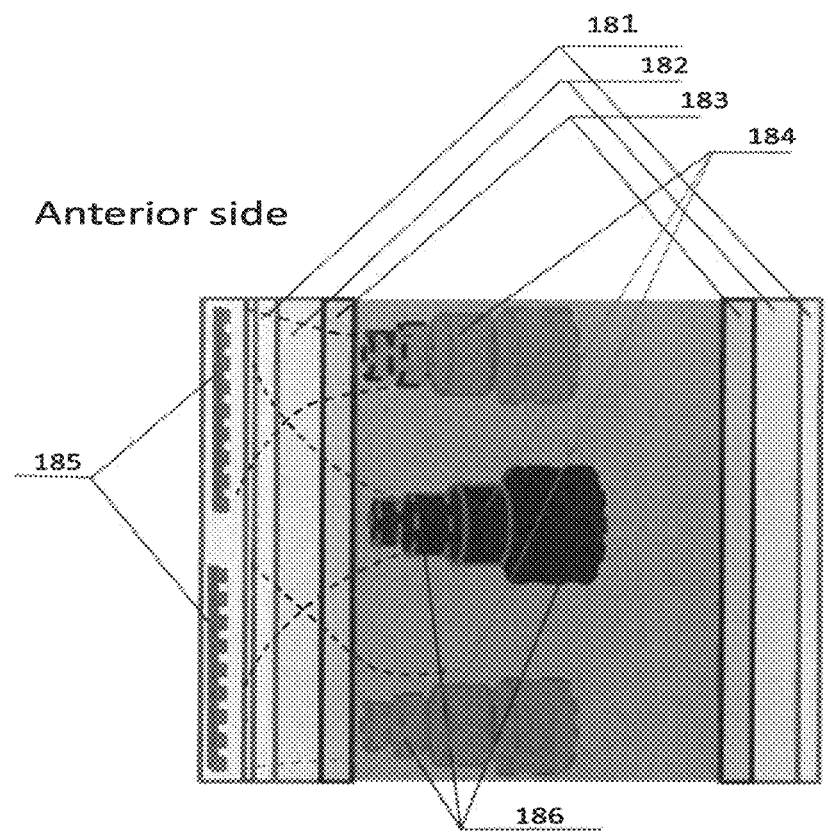

Numerical analysis demonstrates that, for a given antenna size, movement of the focal spot in the organ is accompanied with the changing of the diameter of the focal spot (see Table 3). This variations in the treatment area will cause the change in the power density of irradiation and, therefore, may require the adjustment of the input power, which may be different for different frequencies. Moving the array closer to the skin surface will make a focal distance smaller, and, correspondingly, the diameter of the focal spot smaller, up to a minimum $\lambda_g/3$ [42], which also may be considered during the treatment plan stage. FIG. 18 shows schematically a cross-section of a treatment process of patient lungs infected by a virus using the described embodiment. The NFF antenna array 185 is positioned inside of the bolus vest, which is closely attached to a patient skin 181. Nearest layers of fat 182 and muscles 183 are also shown. The antenna array creates several focal spots 184 inside of the lung volume with EM power density above the threshold value sufficient to destroy a viral capsid. Using a phase and amplitude control of the signal transmitted from sub-arrays and programmed into the Antenna Controller Modem (FIG. 16), the focal spots 184 move inside of the infected organ taking different positions for the predetermined time. Different possible positions 186 of the focal spot are shown in dotted lines. The treatment time is determined depending on the needs of a specific patient and may continue from 15 minutes to an hour.

An apparatus for larynges treatment according to the present invention will now be described.

Figure 19:
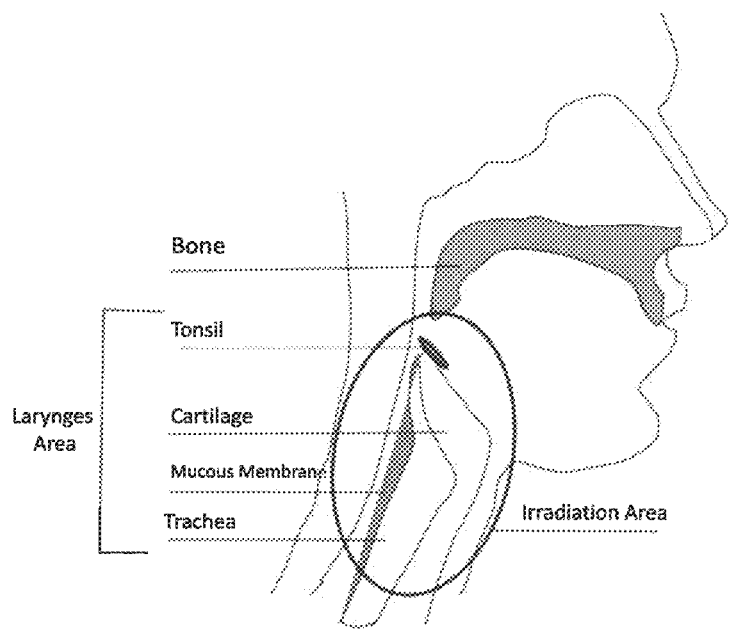

Prior to each treatment, similarly to the lungs treatment procedure, the treatment planning (TP) is required to obtain information about the optimal amplitude and phase settings for each channel in the phased array, and the applicator position around the patient's neck. The anatomy of the treatment area for larynges is shown in FIG. 19.

Analysis of anatomy of an adult patient revealed that the applicator should have a square aperture around 50-60 mm with a bolus for better patient contour conformity. Applying two NFF arrays to two sides of the front area of the neck requires a signal to come through the following body layers structure, shown in the Table 6.

TABLE 6

| | Skin | Muscle | Cartilage | Gland | Mucous Membrane |
|---|---|---|---|---|---|
| Dielectric constant @9.5 GHz, $\varepsilon$ | 31.80 | 43.40 | 26.30 | 46 | 43.40 |
| Thickness, cm | 0.3 | 0.3 | 0.6 | 0.5 | 0.8 |

Figure 20:
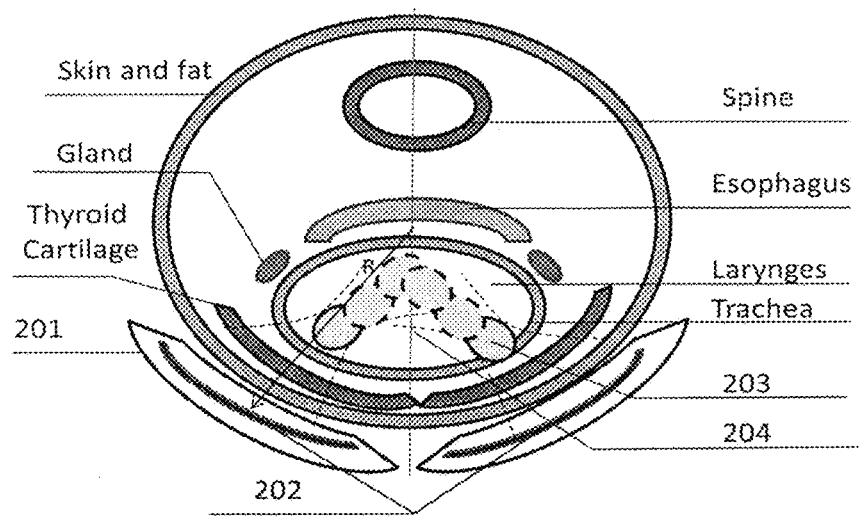

A cross-section of the larynx shown in FIG. 20 demonstrates the operation of the embodiment for larynges treatment for SARS-Cov-19 virus. The larynx area is protected by a cartilage structure called Thyroid Cartilage. Inside of this area there are different glands and mucous membrane, which COVID virus typically infects. The active parts of the embodiment consist of two boluses, which are curved to closely envelop the patient's neck. Inside of the bolus NFF antenna array is located. A typical diameter of the adult neck is about 12 cm, and therefore a bolus and conformal antenna array curvature radius is approximately 7-8 cm. Making antenna array in cylindrical shape has the advantage of obtaining higher density focal spots, especially at the periphery of the treatment area. Using DBF control allows for a creation of a required focal spot position from a quasi-cylindrical array geometry by setting the correct phase in the radiators including the array geometry.

The inter-element spacing of arrays 202 in FIG. 20 is $d=0.8\lambda$ and the array size is $L \times L = 6.4\lambda \times 6.4\lambda$ at the mid-band or approximately 7 cm. The arrays are placed inside of the water bolus 201 for surface layers of the body protection from overheating. The focal distance of the focal spot 203 is varied by a baseband array controller and the phase of the array excitation has been calculated by using the conjugate phase approach. Different positions of the focal spot inside of the larynges volume are shown by dotted line. The EM field density is also indicated by dotted lines 204. The amplitude tapering may or may not be applied. The converging feature 204 of the radiated beam close to focal plane is apparent from the figure, as well as the expected diverging behavior when moving farther from the array surface. The typical-3 dB focus width at the focal plane is W=1 cm at the mid-band and the depth of focus DoF is approximately 1.5-2 cm.

Figure 21:
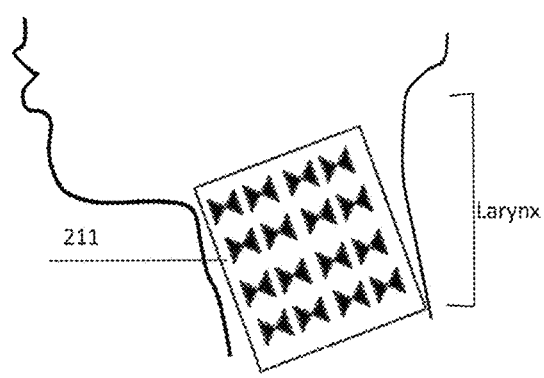

FIG. 21 shows a detail of positioning of NFF antenna array 211 inside of the bolus on the front area of the patient's neck.

Figure 22:
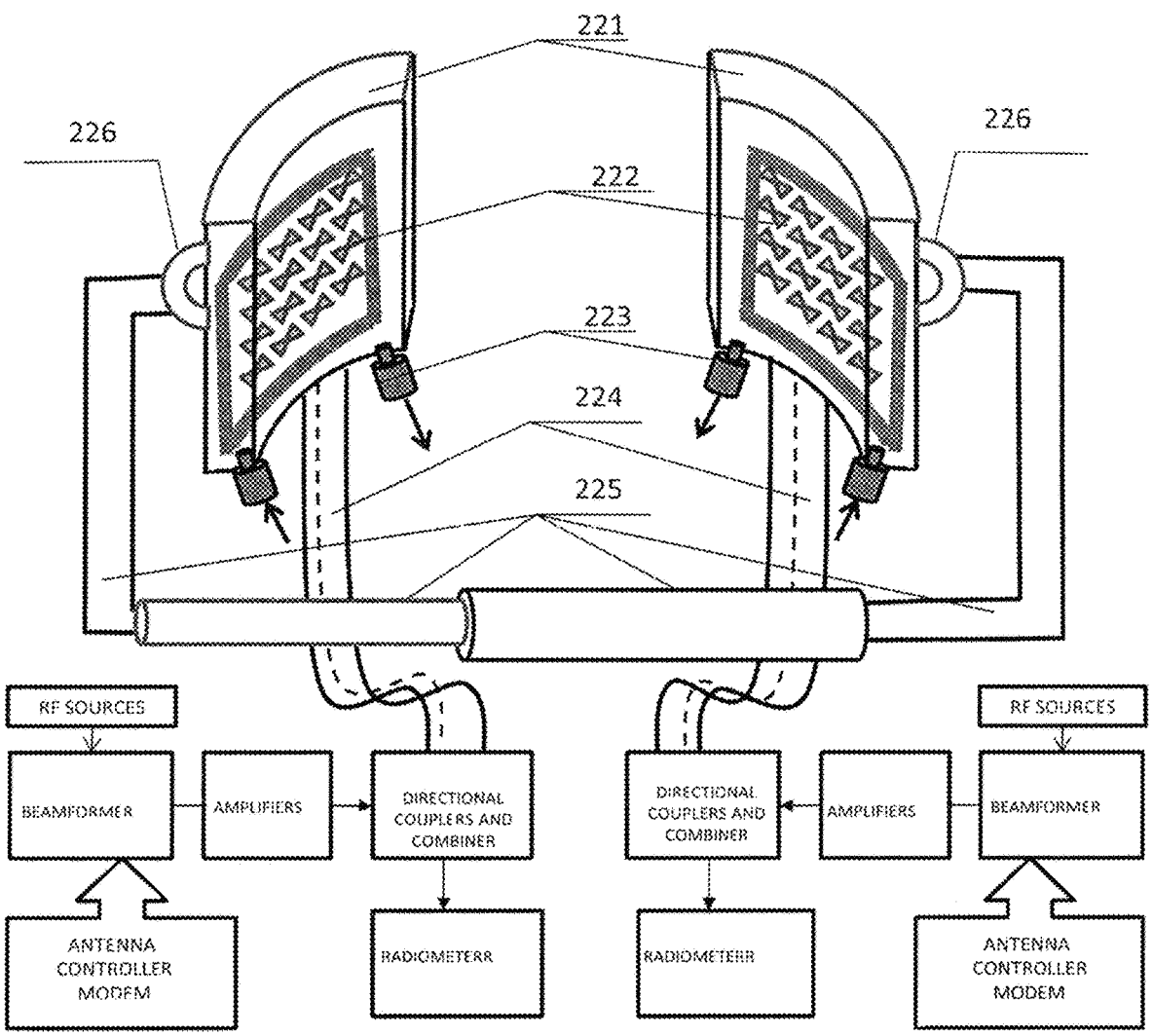

FIG. 22 is a schematic illustration of the antiviral treatment of the larynx area using Non-ionizing Microwave Radiation Therapy. NFF antenna arrays 222 placed inside of the water boluses 221 are positioned at the front of the neck with close proximity to skin surface (FIG. 20). During the therapy session the deionized water is circulated through inlets and outlets 223 of the tubing connected to the boluses. The adjustable frame assembly 225 with ball joints 226 allows for a custom fitting of the bolus-array assemblies 221 and 222 around the neck of the patients. NFF antenna arrays 222 are connected to the control rack with a microwave, baseband and digital equipment via microwave cable assemblies 224, containing 16 coaxial cables attached to each radiator (16 radiators in this exemplary embodiment) to supply a microwave energy with an individual phase and amplitude control for each radiator.

Figure 23:
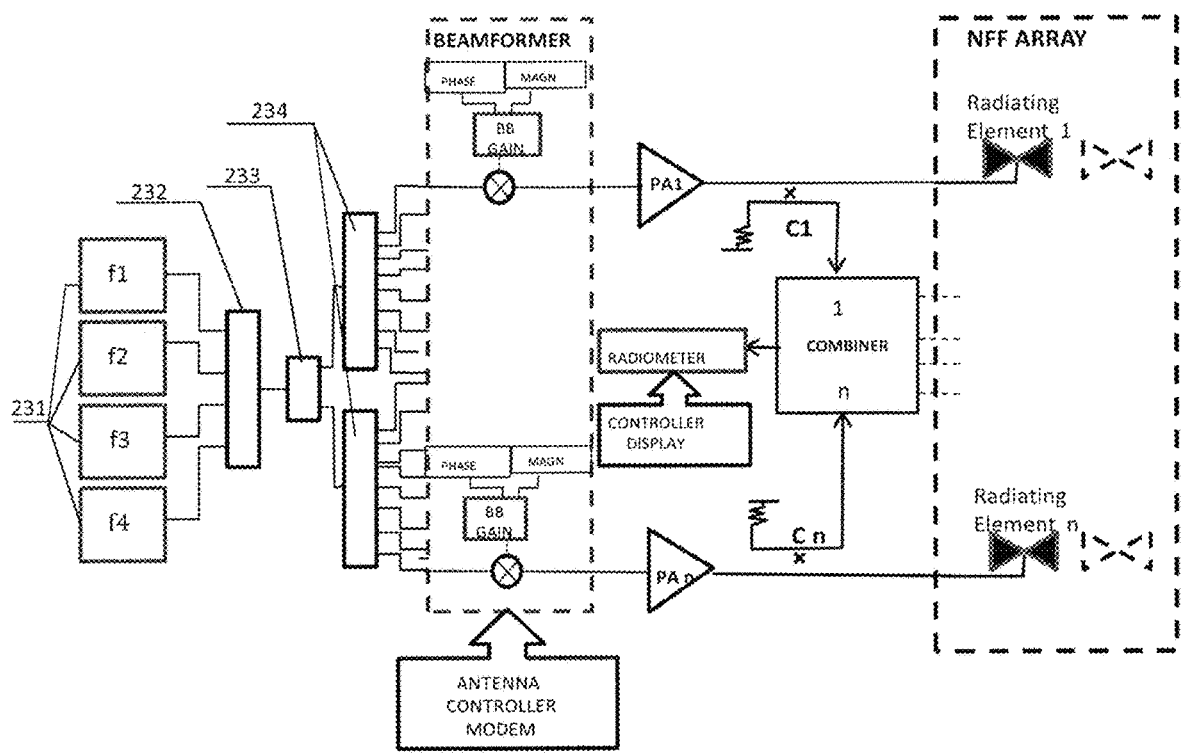

FIG. 22 also shows a slight curvature of conformal antenna arrays around the patient neck for better focusing of microwave energy inside of the larynx area (movement of desirable focal spots locations 203 is shown in FIG. 20).

the organ geometry and time-space information for focal spot locations has been entered into an Antenna Controller Modem shown in FIG. 23.

Considering the anatomy of larynx area, in order to reach a rear mucous membrane area, which is typically get affected by COVID-19 virus, the EM waves must propagate through the thin layers of skin and fat, then thicker layer of thyroid cartilage, and a few centimeters of free space. It results in significantly lower tissue losses than in a lungs irradiation setup and opens up a possibility of using a higher irradiating power density as well as a higher frequency.

Table 7 displays results of approximate calculations for power requirements and a penetration depth for the proposed typical, larynges treatment embodiment with a power density of 14.5 W/m$^2$, which is ten times above the critical value for COVID-19 virus destruction. As reported in [6], this power density level will provide 100% virus inactivation over 15 minutes session.

TABLE 7

| | Frequency, GHz | | | | | | | |
|---|---|---|---|---|---|---|---|---|
| | 9.5 | | 10.5 | | 11.5 | | 12.5 | |
| Tissue | Loss, dB/cm | Loss in Tissue, dB | Loss, dB/cm | Loss in Tissue, dB | Loss, dB/cm | Loss in Tissue, dB | Loss, dB/cm | Loss in Tissue, dB |
| Skin | 7 | 2.1 | 8 | 2.4 | 10 | 9 | 12 | 21.6 |
| Fat | 7 | 0.7 | 8 | 0.8 | 16 | 4.8 | 18 | 10.8 |
| Cartilage | 25 | 15 | 30 | 18 | 35 | 21 | 40 | 24 |
| Propagation Loss to Mucous Membrane Layer | | 17.8 | | 21.2 | | 34.8 | | 56.4 |
| Maximum Mucous Membrane EM Energy Penetration, cm | | 1.55 | | 1.34 | | 0.85 | | 0.3 |

A focal spot control is provided using similar method implemented for lungs treatment embodiment and shown in detail in FIG. 23.

The patient can sit in a chair or lay down on a bed with an antenna arrays holding fixture 225 (FIG. 22) positioned on the neck larynges areas to irradiate the internal volume. "N" individual radiating elements are connected to "N" exciters (Power Amplifiers $PA_1$-$PA_n$) through the cable assembly 224 (FIG. 22), feeding each radiating element from its exciter. In this preferred embodiment N=16. For better treatment efficiency, four microwave sources 231 (FIG. 23) operating with different frequencies located inside or the virus Acoustic Resonance Frequency Band combined via 4:1 power combiner and connected to 1:16 power divider assembly consisting from 1:2 power divider 233 and two 1:8 power dividers 234 are utilized. Other combining/dividing microwave energy methods can be used to achieve the goal that the same broad band microwave energy will be present at each radiating element. Individual radiating elements are broad band antennas of bow-tie type, which have an advantage to be easily integrated in microstrip conformal array with a semi-cylindrical shape.

Other type broad band microstrip radiating elements can be used. The array control is realized using individual Base Band Digital controllers marked BEAMFORMER in FIG. 23 for each radiating element. This technology provides significant freedom in creating the focal spot at the preprogrammed location inside of the organ. Location, timing, and movement of the focal spot are determined in the Treatment Plan initial stage (Step 1 in FIG. 4). The information about Data in Table 7 was estimated for an input power from each frequency source for one array equal to 100 W with a water bolus heat transfer equal 300 W/m$^2$/K. This data demonstrates that with a proper bolus design the input power for lower frequencies 9.5 GHz and 10.5 GHz can be lower than 100 W to guarantee enough penetration into a gland or mucous membrane of 0.5 cm. Correspondingly, with higher bolus heat transfer parameter even higher frequencies can be used in this embodiment for a better efficiency in virus destruction.

Figure 24:
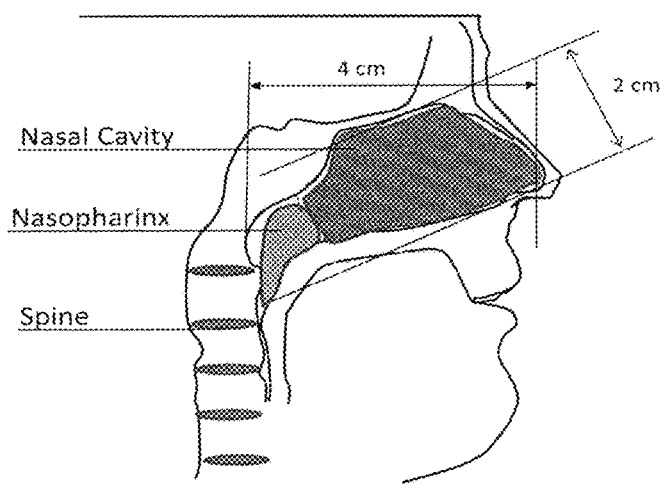
Figure 25:
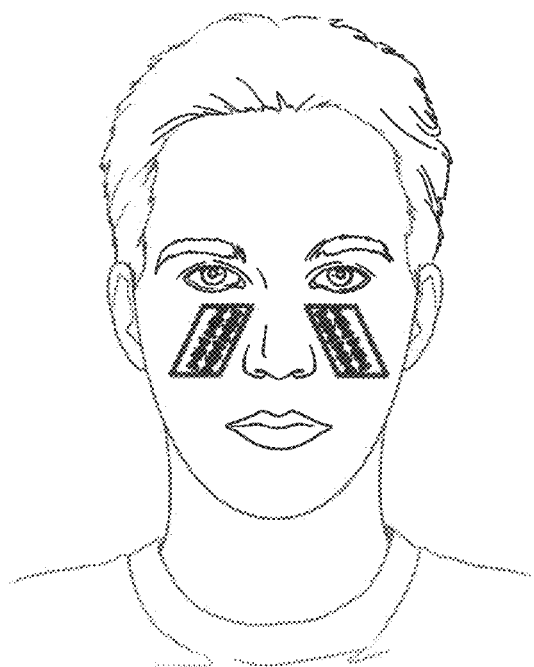
Figure 26:
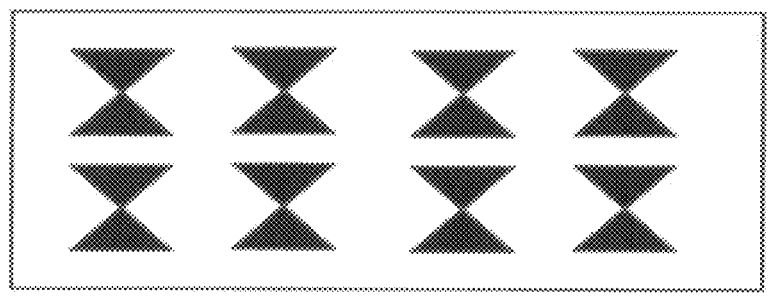

A nasal cavity and nasopharinx area treatment embodiment according to the present invention is described in detail below. The third area that require early treatment for COV-2-SARS viral infection is nasal cavity and nasopharinx area. Anatomy of this part of the body is shown in FIG. 24. FIG. 24 shows a cross-section of the head orifices with desirable areas of irradiation approximately 2×4 cm. Irradiation of the mucous membrane inside of the nasal cavity and nasopharinx can be made from two sides using two rectangular microstrip arrays positioned on the patient's face. The position of irradiating arrays on the face of the patient is shown in FIG. 25. It can use a similar adjustable fixture that is used for the larynges treatment, but with different (smaller) NFF arrays. The shape of the array is dictated by the anatomy of the organ under the treatment, and for the typical adult nasofarinaes case the outline size of the microstrip array is 3 cm×6 cm. The printed circuit board with broad band radiating elements is shown in FIG. 26.

Figure 27:
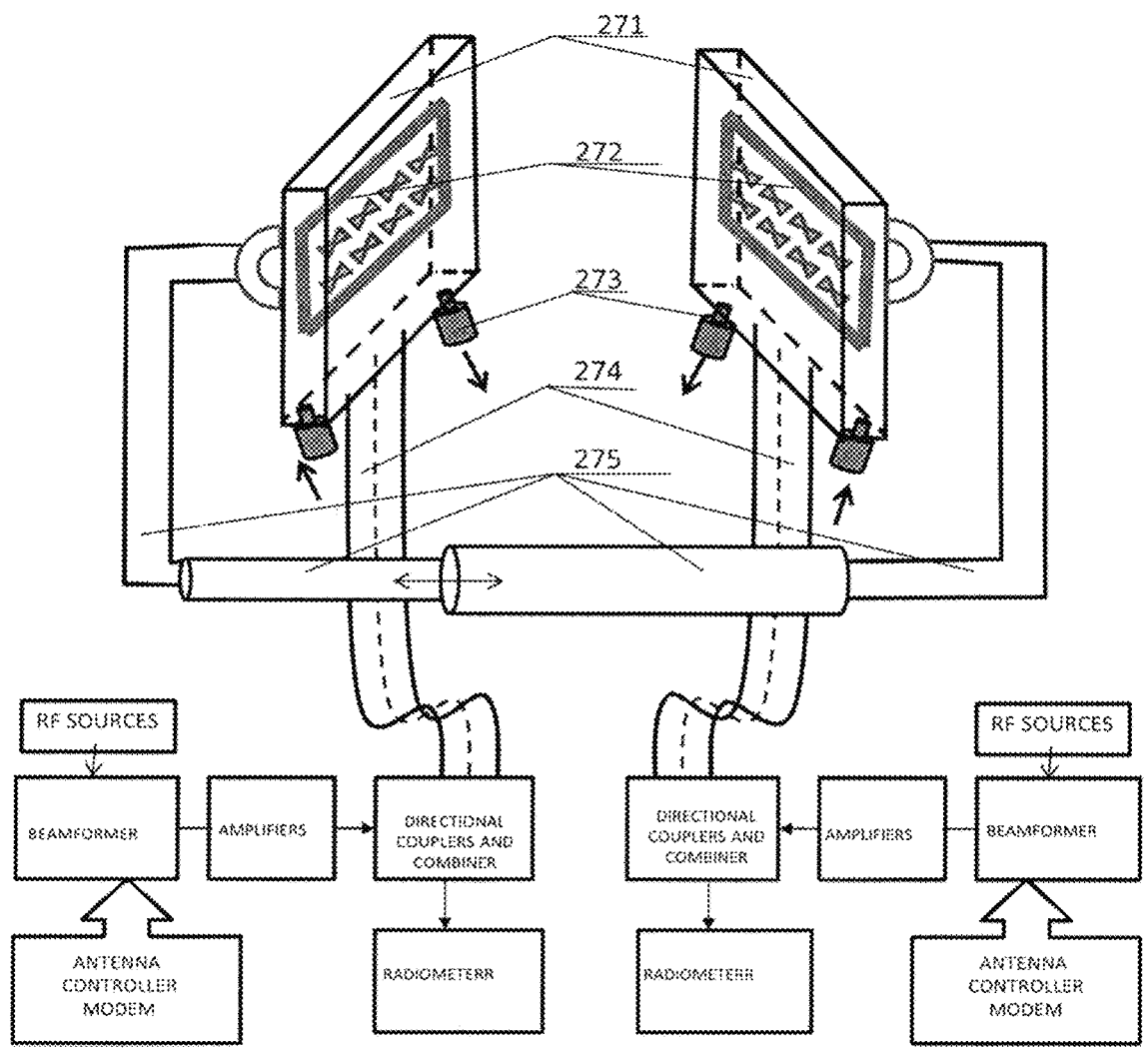

FIG. 27 is an illustration of the set up for treatment of patients with nasal cavities and nasofaringes infected with COVID-19 virus. The NFF arrays 272 designed to fit the patient organs anatomy are placed inside of the water boluses 271 which are attached using ball joints 276 to an adjustable frame 275 to accommodate patients with different facial anatomy.

NFF antenna arrays 272 are connected to the control rack with the microwave, baseband and digital equipment via microwave cable assemblies 224, containing 8 coaxial cables connected to each radiator (8 radiators in this exemplary embodiment) for individual phase and amplitude control of EM waves and controlled focal spot location movement inside of the nasal cavity and nasofarinx area. Table 8 shows typical values expected for a setup position in FIG. 25 used for the nasofarinx treatment. The assumed values are typical for an adult male. Naturally, they will be different for a female or a child and have to be considered at the planning stage for each individual patient (Step 2 in FIG. 4).

TABLE 8

| | Frequency, GHz | | | | | | | |
|---|---|---|---|---|---|---|---|---|
| | 9.5 | | 10.5 | | 11.5 | | 12.5 | |
| Tissue | Loss, dB/cm | Loss in Tissue, dB | Loss, dB/cm | Loss in Tissue, dB | Loss, dB/cm | Loss in Tissue, dB | Loss, dB/cm | Loss in Tissue, dB |
| Skin | 7 | 2.1 | 8 | 2.4 | 10 | 9 | 12 | 21.6 |
| Fat | 7 | 0.7 | 8 | 0.8 | 16 | 4.8 | 18 | 10.8 |
| Cartilage | 25 | 15 | 30 | 18 | 35 | 21 | 40 | 24 |
| Propagation Loss to Mucous Membrane Layer | | 17.8 | | 21.2 | | 34.8 | | 56.4 |
| Maxim Mucous Membrane EM Energy Penetration, cm | | 1.4 | | 1.12 | | 0.66 | | 0.1 |

Because of the smaller size and, therefore the lower antenna gain the penetration into the mucous membrane for nasofaringes treatment is less, which can be compensated by using a higher power for a higher frequency and bolus adjustment, if needed. The present invention is not limited to the details shown since various modifications and structural changes are possible without departing from the spirit of the invention. What is desired to be protected by Letters Patent is set forth in particular in appended claims.

What we claim is:

1. A method for treatment of a patient infected with a virus type having an acoustic resonant frequency in a microwave band 3 GHz-100 GHz, comprising:
   identifying the virus type which infected the patient;
   determining an acoustic resonant frequency or an acoustic resonant frequency range corresponding to the identified virus type;
   designating a patient's organ for treatment and identifying a threshold field strength and a power density required for at least a partial destruction of a viral load of the identified virus type in the patient's organ;

mapping the patient's organ designated for the treatment and using mapping results for programming a beam-forming antenna array;

developing a model for the organ designated for the treatment;

moving a focal spot of the beam-forming antenna array over at least a partial volume of the organ based on the mapping results;

irradiating the at least partial volume of the organ with microwaves having sufficient field strength and power density in the focal spot for the at least partial destruction of the identified virus type in the patient's organ and controlling, with a microwave radiometer connected to the beam-forming antenna array or to a separate near-field-focused (NFF) antenna array, the field strength and the power density such that a temperature at tissue layers of the organ designated for treatment to prevent overheating of surrounding tissues around the irradiated at least partial volume does not exceed a safety level to prevent overheating of surrounding tissue.

2. The method according to claim 1, wherein the virus type is a virus selected from the group consisting of an influenza A virus, an enterovirus EV71, and a plelomorphic Coronavirus SARS-Cov-2.

3. The method according to claim 1, and further comprising using different beam-forming antenna arrays for targeting different organs selected from the group consisting of lungs, larynx, and nasal cavities.

4. The method according to claim 3, wherein the beam-forming antenna array targeted for larynges or nasal cavities comprise conformal microwave radiators with or without Near Field Focus.

5. The method according to claim 1, and further comprising transmitting with the beam-forming antenna array electromagnetic waves with a linear polarization or a circular polarization, depending on a type and a shape of the virus.

6. The method according to claim 1, further comprising connecting the beam-forming antenna array to a microwave power source with operating parameters suitable to attain the suitable field strength and power density.

7. The method according to claim 1, further comprising monitoring the temperature of a treatment spot of the organ designated for treatment with a microwave radiometer receiver with an absorption peak using Planck's Law of Black Body Radiation; and coupled to the beam-forming antenna array so as to be steered at the same area of the organ as the beam-forming antenna array and controlling the irradiating power such that a temperature at tissue layers around the treatment spot does not to exceed safety level.

8. The method according to claim 1, and further comprising selecting a microwave source frequency causing a maximum Structure Resonant Energy Transfer that results in a high amplitude of confined acoustic vibrations in the infecting virus causing its destruction.

9. The method according to claim 1, and further comprising using a Finite Difference Time Domain method for positioning the focal spot for treatment of the infected organ.

10. The method according to claim 1, further comprising using an electromagnetic power source which produces a variable frequency sweep around a central frequency that will cause a movement of the focal spot of the antenna array to irradiate different parts of the infected organ.

* * * * *